US009045539B2

(12) United States Patent
Luehrsen et al.

(10) Patent No.: US 9,045,539 B2
(45) Date of Patent: Jun. 2, 2015

(54) ANTI-EMR1 ANTIBODIES

(75) Inventors: Kenneth Luehrsen, South San Francisco, CA (US); Mark Baer, South San Francisco, CA (US); Christopher R. Bebbington, South San Francisco, CA (US); David Martinez, South San Francisco, CA (US); Varghese Palath, South San Francisco, CA (US); Swathi Sujatha-Bhaskar, South San Francisco, CA (US); Nenad Tomasevic, South San Francisco, CA (US); Jason Williams, South San Francisco, CA (US); Geoffrey T. Yarranton, South San Francisco, CA (US)

(73) Assignee: Kalobios Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/480,937

(22) Filed: May 25, 2012

(65) Prior Publication Data
US 2013/0064826 A1    Mar. 14, 2013

Related U.S. Application Data

(60) Provisional application No. 61/491,095, filed on May 27, 2011.

(51) Int. Cl.
 A61K 39/395 (2006.01)
 G01N 33/566 (2006.01)
 C07K 16/28 (2006.01)
 A61K 39/00 (2006.01)

(52) U.S. Cl.
 CPC ............ *C07K 16/28* (2013.01); *A61K 2039/505* (2013.01); *C07K 2317/24* (2013.01); *C07K 2317/34* (2013.01); *C07K 2317/732* (2013.01)

(58) Field of Classification Search
 None
 See application file for complete search history.

(56) References Cited

U.S. PATENT DOCUMENTS 5,714,350 A * 2/1998 Co et al. ................. 435/69.6
2006/0002923 A1   1/2006 Uede et al.

FOREIGN PATENT DOCUMENTS

WO    WO 2007/064919 A2    6/2007

OTHER PUBLICATIONS

Antibody Information—Definition of Antibodies. www.scbt.com/antibody.html; printed Mar. 11, 2014.*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
International Search Report from PCT/US2012/039717, dated Jan. 10, 2013 (5 pages).
Abnova Datasheet, "EMR1 purified MaxPab mouse polyclonal antibody (B01P)," May 19, 2010 (2 pages).
Hamann et al.; "EMR1, the human homolog of F4/80, is an eosinophil-specific receptor"• *Eur. J. Immunol.*; 37:2797-2802 (2007).

* cited by examiner

*Primary Examiner* — Brian J Gangle
*Assistant Examiner* — Andrea McCollum
(74) *Attorney, Agent, or Firm* — Kilpatrick Townsend & Stockton LLP

(57) ABSTRACT

The invention provides anti-EGF-like module containing, mucin-like, hormone receptor-like 1 (EMR1) antibodies and methods of using such antibodies to treat EMR1-related diseases.

10 Claims, 10 Drawing Sheets

Figure 1

(SEQ ID NO:1)   EVQLVESGGGVVQPGRSLRLSCVVSGFTLIDFGIHWVRQAPGKGLEWVAVIWSGGSTDYADSVKGRFTISRDNSKNTVYLRMNSLRAEDTEVYYCVSIYRGFDSWGQGTTVTVSS
(SEQ ID NO:2)   QVQLVESGGGVVQPGRSLRLSCAASGFSLTSFGIHWVRQAPGKGLEWVGVIWSGGSTNYADSVKGRFTISRDNSKNTVYLRMNSLRAEDTAVYYCVSIYYRGFDSWGQGTTVTVSS
(SEQ ID NO:3)   QVQLVESGGGVVQPGRSLRLSCAVSGFSLITNFGMHWVRQAPGKGLEWVGVIWSGGSTYYADSVKGRFTISRDNSKNTVYLRMNSLRAEDTAVYYCVSIYYRGFDSWGQGTTVTVSS
(SEQ ID NO:4)   QVQLVESGGGVVQPGRSLRLSCAVSGFSLTSFGMHWVRQAPGKGLEWVGVIWSGGSTYYADSVKGRFTISRDNSKNTVYLQMNSLRAEDTAVYYCVSIYYRGFDQWGQGTTVTVSS
(SEQ ID NO:5)   QVQLVESGGGVVQPGRSLRLSCAVSGFSLINFGMHWVRQAPGKGLEWVGVIWSGGSTYYADSVKGRFTISRDNSKNTVYLQMNSLRAEDTAVYYCASIYYRGFDQWGQGTTVTVSS
(SEQ ID NO:6)   QVQLVESGGGVVQPGRSLRLSCAASGFSLTNFGMHWVRQAPGKGLEWVAVIWSGGSTYYADSVKGRFTISRDNSKNTVYLQMNSLRAEDTAVYYCASIYYRGFDVWGQGTTVTVSS
(SEQ ID NO:7)   QVQLVESGGGVVQPGRSLRLSCAASGFSLTSFGMHWVRQAPGKGLEWVAVIWSGGSTYYADSVKGRFTISRDNSKNTVYLQMNSLRAEDTAVYYCASIYYRGFDVWGQGTTVTVSS
(SEQ ID NO:8)   QVQLVESGGGVVQPGRSLRLSCAVSGFSLTSFGMHWVRQAPGKGLEWVAVIWSGGSTYYADSVKGRFTISRDNSKNTVYLQMNSLRAEDTAVYYCASIYYRGFDVWGQGTTVTVSS
(SEQ ID NO:9)   QVQLVESGGGVVQPGRSLRLSCAVSGFSLTSFGMHWVRQAPGKGLEWVAVIWSGGSTYYADSVKGRFTISRDNSKNTVYLQMNSLRAEDTAVYYCASIYYRGFDQWGQGTTVTVSS
(SEQ ID NO:10)  QVQLVESGGGIVQPGGSLRLSCAASGFSLTSFGMHWVRQAPGKGLEWVAVIWSGGSTYYADSVKGRFTISRDNSKNTVYLRMNSLRAEDTAVYYCVSIYYRGFDSWGQGTTVTVSS
(SEQ ID NO:11)  QVQLVESGGGVVQPGRSLRLSCAVSGFSLTSFGMHWVRQAPGKGLEWVAVIWSGGSTYYADSVKGRFTISRDNSKNTVYLQMNSLRAEDTAIYYCASIYYRGFDQWGQGTTVTVSS (SEQ ID NO:12)  DVVMTQSPLSLPVTPGEPASISCKSSQSLVHSNGNNYLEWYLQKPGQSPQLLIYRGSNRASGVPDRFSGSGSGTDFTLKISRVEAEDVGVYYCFQGSHVPLTFGQGTRLEIK
(SEQ ID NO:13)  DVVMTQSPLSLPVTPGEPASISCRSSQSLLHSNGYTYLEWYLQKPGQSPQLLIYRGSNRASGVPDRFSGSGSGTDFTLKISRVEAEDVGVYYCFQGSHVPLTFGQGTRLEIK
(SEQ ID NO:14)  DIVMTQSPLSLPVTPGEPASISCRSSQSLLHSNGYTYLEWYLQKPGQSPQLLIYRGSNRASGVPDRFSGSGSGTDFTLKISRVEAEDVGVYYCFQGSHVPLTFGQGTRLEIK
(SEQ ID NO:15)  DIVMTQSPLSLPVTPGEPASISCRSSQSILHSNGYTYLEWYLQKPGQSPQLLIYRGSNRASGVPDRFSGSGSGTDFTLKISRVEAEDVGVYYCVQGGHLPLTFGQGTRLEIK
(SEQ ID NO:16)  DIVMTQSPLSLPVTPGEPASISCRSSQSILHSNGYTYLEWYLQKPGQSPQLLIYRGSMRASGVPDRFSGSGSGTDFTLKISRVEAEDVGVYYCVQGTHVPLTFGQGTRLEIK
(SEQ ID NO:17)  DIVMTQSPLSLPVTPGEPASISCRSSQSLVHSNGNTYLEWYLQKPGQSPQLLIYRVSNRASGVPDRFSGSGSGTDFTLKISRVEAEDVGVYYCVQGTHVPLTFGQGTRLEIK
(SEQ ID NO:18)  DIVMTQSPLSLPVTPGEPASISCRSSQSLVHSNGNTYLEWYLQKPGQSPQLLIYRVSNRASGVPDRFSGSGSGTDFTLKISRVEAEDVGVYYCVQGTHVPLTFGQGTRLEIK
(SEQ ID NO:19)  DIVMTQSPLSLPVTPGEPASISCRSSQSLLHSNGYTYLEWYLQKPGQSPQLLIYRGSNRASGVPDRFSGSGSGTDFTLKISRVEAEDVGVYYCTQGSHVPLTFGQGTRLEIK
(SEQ ID NO:20)  DIVMTQSPLSLPVTPGEPASISCRSSQSILHSNGYTYLEWYLQKPGQSPQLLIYRGSNRASGVPDRFSGSGSGTDFTLKISRVEAEDVGVYYCFQGSHVPLTFGQGTRLEIK
(SEQ ID NO:21)  DIFMTQSPLSLPVTPGEPASISCRSSQSLVHSNGNTYLEWYLQKPGQSPQLLIYRVSNRASGVPDRFSGSGSGTDFTLKISRVEAEDVGVYYCVQGTHVPLTFGQGTRLEIK
(SEQ ID NO:22)  DIFMTQSPLSLPVTPGEPASISCRSSQSLVHSNGYTYLEWYLQKPGQSPQLLIYRVSNRASGVPDRFSGSGSGTDFTLKISRVEAEDVGVYYCVQGTHVPLTFGQGTRLEIK

*Figure 1—con't*

| Fab | Heavy chain Seq# | % Identity to human germline for Vh segment versus Vh3-33 | Light chain seq# | % Identity to human germline for Vk segment versus VkII A3 | % Identity to human germline for Vh and Vk segments |
|---|---|---|---|---|---|
| EM279-1 | 8 | 89 | 17 | 93 | 91 |
| EM289-2 | 4 | 88 | 17 | 93 | 90 |
| EM300-1 | 9 | 89 | 17 | 93 | 91 |
| EM302-2 | 9 | 89 | 18 | 94 | 91 |
| EM259-3F | 6 | 89 | 15 | 95 | 92 |
| EM259-7G | 7 | 90 | 16 | 97 | 93 |
| EM312-1 | 11 | 88 | 21 | 92 | 90 |
| EM313-3 | 11 | 88 | 22 | 93 | 90 |
| EM314-2 | 9 | 89 | 21 | 92 | 90 |
| EM315-2 | 11 | 88 | 17 | 93 | 90 |

% identity values for the light chain exclude the V-segment sequence within the LCDR3
% identity values rounded to nearest integer
Deletions count as one change

Figure 2

| Sequence Annotation | Position | Length | Description |
|---|---|---|---|
| Signal Peptide | 1-20 | 20 | Cytoplasmic |
| Topological domain | 21-599 | 579 | Extracellular |
| Transmembrane | 600-627 | 28 | Helical; Name=1 |
| Domain | 31-79 | 49 | EGF-like 1 |
| Domain | 80-131 | 52 | EGF-like 2; calcium-binding |
| Domain | 132-171 | 40 | EGF-like 3; calcium-binding |
| Domain | 172-220 | 49 | EGF-like 4; calcium-binding |
| Domain | 221-267 | 47 | EGF-like 5; calcium-binding |
| Domain | 268-316 | 49 | EGF-like 6; calcium-binding |
| Domain | 547-596 | 50 | GPS |
| Compositional bias | 317-599 | 283 | Ser/Thr-rich |
| Transmembrane | 748-776 | 29 | Helical; Name=5 |
| Topological domain | 777-794 | 18 | Cytoplasmic |
| Transmembrane | 795-814 | 20 | Helical; Name=6 |
| Topological domain | 815-829 | 15 | Extracellular |
| Transmembrane | 830-852 | 23 | Helical; Name=7 |
| Topological domain | 853-886 | 34 | Cytoplasmic |

Figure 8

A. REF HCDR3      IYYRGFDS          B. REF LCDR3      FQGSHVPLT
   EM251-3-10A    IYYRGFD*Q*           EMX-11A        FQGSH*PP*LT
   EM259-3F       IYYRGFD*V*           EMX-5D         FQG*V*HVPLT
   EM269-10E      IYYRGFD*K*           EM251-3-10A    *T*QGSHVPLT
                                       EM251-3-11G    *N*QGSHVPLT
                                       EM259-3F       *V*QG*G*HLPLT
                                       EM259-7G       *V*QG*T*HVPLT

US 9,045,539 B2

ANTI-EMR1 ANTIBODIES

CROSS-REFERENCE TO RELATED APPLICATIONS

This application claims benefit of U.S. provisional application No. 61/491,095, filed May 27, 2011, which is incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -41-1.TXT, created on May 1, 2013, 57,344 bytes, machine format IBM-PC, MS-Windows operating system, is hereby incorporated by reference in its entirety for all purposes.

BACKGROUND OF THE INVENTION

The receptor EGF-like module containing, mucin-like, hormone receptor-like 1 (EMR1) is expressed on human eosinophilic granulocytes, but not on other leukocytes, including basophils, monocytes, macrophages and myeloid dendritic cells. EMR1 belongs to the EGF-TM7 family, a subfamily within the adhesion class of TM7 proteins. Other EGF-TM7 family members include CD97 and EMR2, EMR3, and EMR4. Eosinophils are involved in the pathogenesis of allergic disease and various inflammatory disorders, and increasing blood and tissue eosinophilia is related to the presence and severity of symptoms. Thus, EMR1 is a desirable therapeutic target for diseases in which eosinophils play a role in the pathology of the disease.

Antibodies that bind to EMR1 are known (see, e.g., Hamann et al., *Eur. J. Immunol.* 37:2797-2802, 2007). However, there is a need for the development of therapeutic antibodies that selectively target EMR-1 and deplete eosinophils. This invention addresses that need.

BRIEF SUMMARY OF THE INVENTION

The invention is based, in part on the discovery of new anti-EMR1 antibodies that selectively bind to EMR1. Thus, in one aspect, the invention provides an isolated anti-EMR1 antibody that selectively binds to epidermal growth factor-like domain-6 (ELD-6) of EMR1. In some embodiments, the antibody competes with an antibody having a $V_H$ and $V_L$ sequence of monoclonal antibody 1E7 (SEQ ID NOS:23 and 24, respectively) for binding to EMR1. In some embodiments, the antibody binds to all, or a portion of, the EMR1 sequence RDIDECRQDPSTCGPNSI (SEQ ID NO:30).

In some embodiments, an anti-EMR1 antibody of the invention comprises a $V_H$ CDR3 amino acid sequence IYYRGFDX$_1$ (SEQ ID NO:31), wherein X$_1$ is Q, S, K, or V. In some embodiments, the antibody comprises a $V_H$ CDR3 amino acid sequence IYYRGFDX$_1$ (SEQ ID NO:32), wherein X$_1$ is Q, S, or V. In some embodiments, the antibody further comprises a $V_H$ CDR1 that has an amino acid sequence (D/S/N)FG(M/I)H (SEQ ID NO:33) and/or a VH CDR2 that has an amino acid sequence VIWSGGST(D/N/Y)YADSVKG (SEQ ID NO:34). In some embodiments, the $V_H$ has a V-segment amino acid sequence set forth in FIG. 1. In some embodiments, the antibody has a $V_H$ that has the amino acid sequence of a $V_H$ region set forth in FIG. 1.

In some embodiments, an anti-EMR1 antibody of the invention comprises a $V_L$ CDR3 amino acid sequence (F/V/T/N)QG(V/S/G/T)H(V/L/P)PLT (SEQ ID NO:35). In some embodiments, the antibody comprises a $V_L$ CDR3 amino acid sequence (F/V/T)QG(S/G/T)H(V/L)PLT (SEQ ID NO:36). In some embodiments, the $V_L$ comprises a CDR1 that has an amino acid sequence (R/K)SSQS(I/L)(V/L)HSNG(N/Y)(N/T)YLE (SEQ ID NO:37) and/or a CDR2 that has an amino acid sequence R(V/G)SNRAS (SEQ ID NO:38). In some embodiments, the $V_L$ has a V-segment amino acid sequence set forth in FIG. 1. In some embodiments, the antibody has a $V_L$ that has the amino acid sequence of a $V_L$ region set forth in FIG. 1.

The invention additionally provides an anti-EMR1 antibody that has a heavy chain and a light chain variable region that, when excluding the CDR3, has at least 80%, typically at least 90%, or greater, sequence identity to human germline sequences. Thus, such an antibody may have, e.g., a $V_H$ that has at least 80%, or at least 85%, 86%, 87%, 88% or 89%; and typically at least 90%, 91%, 92%, 93%, 94%, 95%, 96%, 97%, 98% or 99% identity, to a human germline $V_H$ V-segment and an FR4 that is at least 85% or at least 90% identical to the FR4 of a human JH segment; and a $V_L$ that has at least 80% or at least 85%, 86%, 87%, 88%, or 89%; and Typically at least 90%, 91%, 92%, 93%, 94%, 95%, 96%, 97%, 98% or 99% identity, to a human germline V kappa or V lambda V-segment and an FR4 that is at least 85% or at least 90% identical to the FR4 of a human Jkappa or Jlambda segment.

The invention also provides an anti-EMR1 antibody that has a heavy chain and a light chain, wherein the heavy chain variable region has a sequence set forth in FIG. 1.

In some embodiments, an anti-EMR1 antibody that has a heavy chain and a light chain, wherein the light chain variable region has a sequence set forth in FIG. 1.

In some embodiments, an anti-EMR1 antibody of the invention has a $V_H$ region and a $V_L$ region that comprises the following sequences: SEQ ID NO:8 and SEQ ID NO:17; SEQ ID NO:4 and SEQ ID NO:17; SEQ ID NO:9 and SEQ ID NO:17; SEQ ID NO:9 and SEQ ID NO:18; SEQ ID NO:6 and SEQ ID NO:15; SEQ ID NO:7 and SEQ ID NO:16; SEQ ID NO:11 and SEQ ID NO:21; SEQ ID NO:11 and SEQ ID NO:22; SEQ ID NO:9 and SEQ ID NO:21; or SEQ ID NO:11 and SEQ ID NO:17.

In some embodiments, an anti-EMR1 antibody of the invention has a $V_H$ region that comprises the amino acid sequence of SEQ ID NO:23 and a $V_L$ region that comprises the amino acid sequence of SEQ ID NO:24.

In some embodiments of an anti-EMR1 antibody of the invention the $V_H$ region or the $V_L$ region, or both the $V_H$ and $V_L$ region amino acid sequences comprise a methionine at the N-terminus.

In some embodiments, an anti-EMR1 antibody of the invention is an IgG, e.g., an IgG1 or IgG3; or an IgG2 or IgG4.

In a further aspect, the invention provides an antibody preparation comprising an anti-EMR1 antibody as described herein, wherein the heavy chain constant region is hypofucosylated or afucosylated.

In some embodiments, an anti-EMR1 antibody of the invention has a $K_D$ of less than about 10 nM. In some embodiments, the antibody has a $K_D$ of less than 1 nM.

In a further aspect, the invention provides a method of depleting eosinophils in a subject, e.g., a human, the method comprising administering a hypofucosylated or fucosylated anti-EMR1 antibody that selectively binds primate eosinophils, e.g., human eosinophils.

In some embodiments, the invention provides a method of decreasing the level of eosinophils in a subject, the method comprising administering an anti-EMR1 antibody of the invention as described herein to the subject, wherein the subject has an EMR1-dependent disease, e.g., a disease selected from the group consisting of chronic obstructive pulmonary disease, chronic eosinophilic pneumonia, asthma, including allergic asthma, allergic bronchopulmonary aspergillosis, allergic colitis, inflammatory bowel disease, coeliac disease, gastroesophageal reflux disease, nasal polyposis, eosinophilic gastroenteritis, eosinophilic gastritis, eosinophilic esophagitis, eosinophilic colitis, Churg-Strauss syndrome, eosinophilic myalgia syndrome, hypereosinophilic syndrome, episodic angiodema, onchocercal dermatitis, atopic dermatitis, eczema, an eosinophilic pulmonary disease that results from helminthic infections, eosinophilic panniculitis, episodic angioedema with eosinophilia (Gleich syndrome), acute eosinophilic interstitial nephritis and renal failure with bone marrow-lymph node granulomas and anterior uveitis, Samter's syndrome, bronchial asthma, intolerance to aspirin, chronic rhinosinusitis, NARES (nonallergic rhinitis with eosinophilia syndrome), drug or toxin-induced pneumonitis, and acute or chronic eosinophilic leukemia. In some embodiments, the subject has chronic obstructive pulmonary disease. In some embodiments an anti-EMR1 antibody of the invention is administered to a subject after nasal polyp removal to prevent or reduce the recurrence of polyps.

In additional aspects, the invention provides methods of monitoring the therapeutic efficacy of treatments for eosinophil-mediated diseases and methods of identifying subjects who are candidates for treatment with a therapeutic method that target eosinophils for depletion. Thus, in some embodiments, the invention provides a method of assessing efficacy of a treatment that targets eosinophils in a patient that has an eosinophil-dependent disease, the method comprising: contacting a biological sample that comprises eosinophils from the patient with an anti-EMR1 antibody that selectively binds to EMR1, e.g., at the ELD-6 domain; detecting the binding of the antibody to eosinophils, and determining the levels of eosinophils, wherein a reduction in the level of eosinophils in the patient compared to the level before treatment is indicative of therapeutic efficacy. The anti-EMR1 antibody can be any anti-EMR1 antibody described herein. In some embodiments, the treatment method that is undergoing evaluation for efficacy is a treatment that comprises administering an anti-EMR1 antibody that selectively binds to eosinophils and mediates antibody-dependent cell-mediated cytotoxicity (ADCC) or complement-dependent cytoxicity (CDC) activity. In some embodiments, the anti-EMR1 antibody is any one of the antibodies of the invention described herein.

The invention additionally provides a method of screening for a patient that has an eosinophil-dependent disease and is a candidate for treatment with a therapeutic agent that depletes eosinophils, the method comprising: contacting a biological sample that comprises eosinophils from the patient with an anti-EMR1 antibody, e.g., that selectively binds ELD-6 of EMR1; detecting the binding of the antibody to eosinophils, and determining the levels of eosinophils in the patient, thereby screening for a patient that is a candidate for the treatment. In typical embodiments, the anti-EMR1 antibody that selectively binds ELD-6 of EMR1 is an antibody of the invention as described herein.

The invention also provides a method of identifying a patient that has an eosinophil-dependent disease and is a candidate for treatment with a therapeutic agent that depletes eosinophils, the method comprising: contacting a biological sample that comprises eosinophils from the patient with an anti-IL-5 receptor antibody; detecting the binding of the antibody to eosinophils, determining the levels of eosinophils in the patient, selecting a patient that has elevated levels of eosinophils compared to normal; and administering a therapeutic anti-EMR1 antibody that selectively binds to eosinophils and mediates ADCC. In typical embodiments, the therapeutic anti-EMR1 antibody is an anti-EMR1 antibody of the invention as described herein.

In other embodiments, the invention provides a method of identifying a patient that has an eosinophil-dependent disease and is a candidate for treatment with a therapeutic agent that depletes eosinophils, the method comprising: determining the level of soluble IL-5 receptor splice variant (sIL-5R) present in a serum sample from the patient; selecting a patient that has elevated levels of sIL-5R compared to normal; and administering an anti-EMR1 antibody that selectively binds to eosinophils and mediates ADCC. The step of determining the level of sIL-5R can be performed using any method that detects sIL-5R protein or nucleic acid in the serum. In some embodiments, the method comprises detecting the level of sIL-5R nucleic acid using an amplification reaction. In some embodiments, the method comprises detecting the level of sIL-5R protein using an immunoassay. In some embodiments, the anti-EMR1 antibody administered to the patient is an anti-EMR1 antibody as described herein.

The invention also provides a method of assessing efficacy of a treatment that comprises administering an anti-EMR1 antibody that selectively binds EMR1 and has ADCC activity to a patient, wherein the method comprises: contacting a biological sample that comprises eosinophils from the patient with an anti-EMR1 antibody of any one of the anti-EMR1 antibodies described herein; detecting the binding of the antibody to eosinophils, and determining the levels of eosinophils, wherein a reduction in the level of eosinophils in the patient compared to the level before treatment is indicative of therapeutic efficacy.

The methods of evaluating efficacy and/or of screening subjects that are candidates for therapies that selectively target eosinophils can be performed on a patient that has any eosinophil-dependent disease. In some embodiments, the patient has chronic obstructive pulmonary disease, chronic eosinophilic pneumonia, asthma, including allergic asthma, allergic bronchopulmonary aspergillosis, allergic colitis, inflammatory bowel disease, coeliac disease, gastroesophageal reflux disease, nasal polyposis, eosinophilic gastroenteritis, eosinophilic gastritis, eosinophilic esophagitis, eosinophilic colitis, Churg-Strauss syndrome, eosinophilic myalgia syndrome, hypereosinophilic syndrome, episodic angiodema, onchocercal dermatitis, atopic dermatitis, eczema, an eosinophilic pulmonary disease that results from helminthic infections, eosinophilic panniculitis, episodic angioedema with eosinophilia (Gleich syndrome), acute eosinophilic interstitial nephritis and renal failure with bone marrow-lymph node granulomas and anterior uveitis, Samter's syndrome, bronchial asthma, intolerance to aspirin, chronic rhinosinusitis, NARES (nonallergic rhinitis with eosinophilia syndrome), drug or toxin-induced pneumonitis, or acute or chronic eosinophilic leukemia.

BRIEF DESCRIPTION OF THE DRAWINGS

FIG. 1 provides examples of amino acid sequences of heavy (SEQ ID NOS:1-11) and light (SEQ ID NOS:12-22) chain variable regions of anti-EMR1 antibodies of the invention. Examples of antibodies are also provided.

FIG. 2 provides a summary of the domain structure of EMR1.

FIG. 3A shows data from supernatants of transient transfections on a colorimetric anti-human Fc Western blot. Both gene constructs, EMR1-ELD and EMR1-ELD-del6, were expressed and expressed protein was transferred onto blot membranes. FIG. 3B shows aliquots of the same supernatants on a blot membrane probed using c1E7 antibody and developed with an ECL substrate. The monoclonal antibody c1E7 does not bind to the deletion mutant as assessed by Western blot analysis, indicating that binding of c1E7 requires ELD-6.

FIG. 8 shows HCDR3 (Panel A; SEQ ID NOS:40, 39, 41 and 42, respectively) and LCDR3 (Panel B; SEQ ID NOS:54, 61, 58, 88, 56, 89 and 62, respectively) affinity maturation changes that support antigen binding. The reference sequences are underlined at top and the CDR3 changes that support antigen binding are in italics.

DETAILED DESCRIPTION OF THE INVENTION

Figure 3:
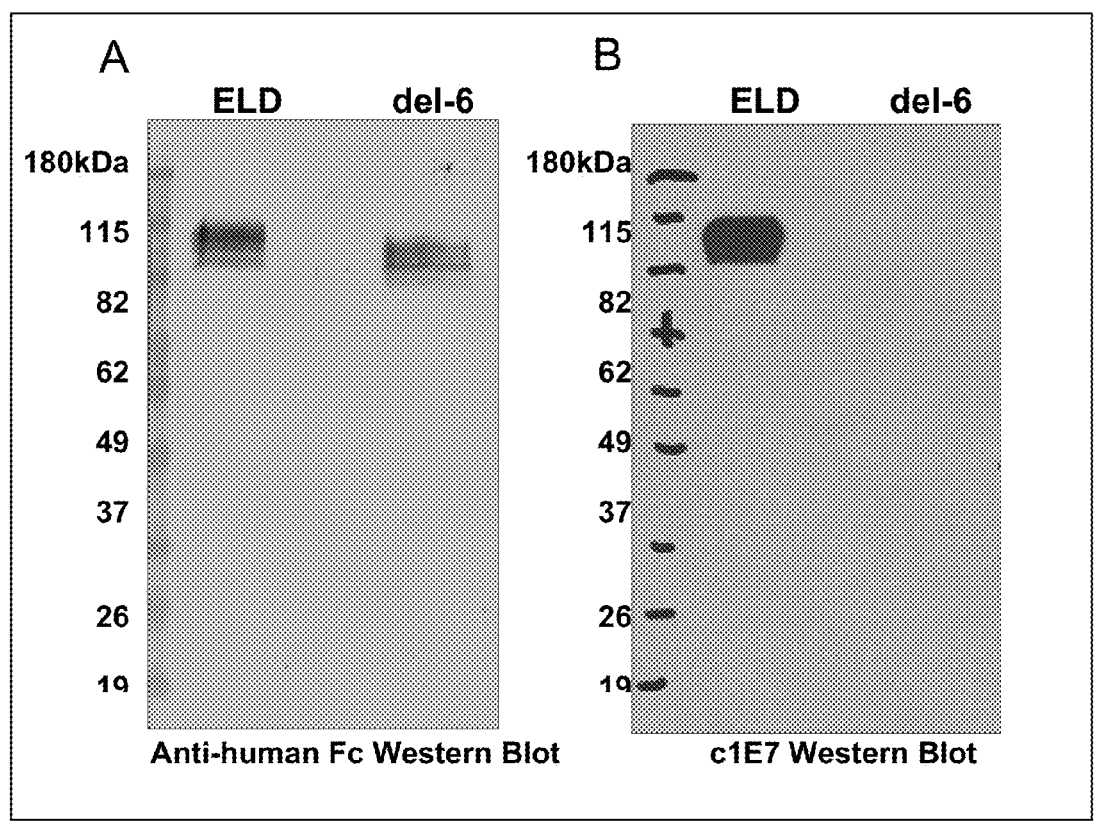
FIGS. 3 A and B provide an example of data showing binding of anti-EMR1 monoclonal antibody c1E7 to an EMR1 EGF-like domain-6 (ELD-6) deletion mutant by Western blot.

As used herein, "EGF-like module containing, mucin-like, hormone receptor-like 1" or "EMR1" refers to a receptor that is a member of the EGF-TM7 family. EMR1 has a domain at the C-terminus that has seven transmembrane regions. The N-terminus of the protein has six EGF-like domains (referred to herein as ELD-1, ELD-2, ELD-3, ELD-4, ELD-5, and ELD-6) which are separated from the transmembrane domain by a serine/threonine-rich domain. The UniProtKB/Swiss-Prot. Identifier for human EMR1 is Q14246. Human EMR1 is localized to 19p13.3. The term "EMR1" includes polymorphic variants that occur at that locus. An example of a human EMR1 extracellular domain protein sequence is provided in SEQ ID NO:25.

In the present invention, "EMR1 antibody" or "anti-EMR1 antibody" are used interchangeably to refer to an antibody that specifically binds to EMR1.

An "antibody having an active isotype" as used herein refers to an antibody that has a human Fc region that binds to an Fc receptor present on immune effector cells. "Active isotypes" include IgG1, IgG3, IgM, IgA, and IgE. The term encompasses antibodies that have a human Fc region that comprises modifications, such as mutations or changes to the sugar composition and/or level of glycosylation, that modulate Fc effector function.

In the present invention, the terms "has ADCC" activity" and "mediates ADCC" are used interchangeably. In the present invention, an antibody that has "enhanced antibody-dependent cell-mediated cytotoxicity" or "enhanced ADCC" refers to an antibody that is modified, such as by oligosaccharide modification or mutation, so that ADCC is increased, e.g., at least 2-fold, typically at least 5-fold and preferably at least 10-fold relative to the antibody prior to modification. ADCC is measured using well known assays. For example, in the present invention, ADCC is typically measured by in vitro assays in which patient-derived or normal peripheral blood-derived effector cells are incubated with eosinophil target cells, at a selected ratio of effector:target cells, usually a ratio between 10 and 100, in the presence of anti-EMR1 antibody. Antibody-dependent cell killing is measured after a period of incubation of generally between 4 and 24 hours, for example, by determining the release of intracellular enzyme such as LDH.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., Science 247:306-1310, 1990).

The term "equilibrium dissociation constant" or "affinity", abbreviated ($K_D$), refers to the dissociation rate constant ($k_d$, time$^{-1}$) divided by the association rate constant ($k_a$, time$^{-1}$ M$^{-1}$). Equilibrium dissociation constants can be measured using any known method in the art. The antibodies of the present invention are high affinity antibodies. Such antibodies have a $K_D$ of less than about 50 nM and often less than about 10 nM as determined by surface plasmon resonance analysis performed at 37° C. Thus, in some embodiments, the antibodies of the invention have a $K_D$ (as measured using surface plasmon resonance) of less than about 50 nM, typically less than about 25 nM, or even less than 10 nM, e.g., about 5 nM or about 1 nM. In the context of the invention, an affinity is "better" if it has a higher affinity, e.g., as evidenced by a lower numerical $K_D$.

The phrase "specifically (or selectively) binds" to an antigen or target or "specifically (or selectively) immunoreactive with," when referring to a protein or peptide, refers to a binding reaction whereby the antibody binds to the antigen or target of interest. In the context of this invention, the antibody binds to EMR1 with an affinity that is at least 100-fold greater than its affinity for other antigens.

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical IgG immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody C-terminal to the disulfide linkages in the hinge region to produce F(ab')$_2$, a dimer of Fab which itself is a light chain joined to VH-CH1 by a disulfide bond. The F(ab')$_2$ may be reduced under mild conditions to break the disulfide linkage in the hinge region thereby converting the F(ab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include $V_H$-$V_L$ dimers, including single chain antibodies in which a variable heavy and a variable light region are joined together (directly or through a peptide linker) to form a continuous polypeptide. Alternatively, the antibody can be another fragment. Other fragments can also be generated, e.g., using recombinant techniques, as soluble proteins or as fragments obtained from display methods. Antibodies thus can also include diantibodies, miniantibodies, and heavy chain dimers, such as antibodies from camelids.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending through FR3 up to CDR3.

As used herein, the term "J-segment" refers to a subsequence of the variable region encoded comprising a C-terminal portion of a CDR3 and the FR4. A germline J-segment is encoded by an immunoglobulin J-gene segment.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl. Acad. Sci. USA,* 86, 9268-9272 (1989); Martin, et al, *Methods Enzymol.*, 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in which CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci. USA* 91: 969, 1994).

A "Humaneered™" antibody in the context of this invention refers to an engineered human antibody having a binding specificity of a reference antibody. A "Humaneered™" engineered human antibody for use in this invention has an immunoglobulin molecule that contains minimal sequence derived from a donor immunoglobulin. Typically, such an antibody is engineered by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. Such methods are described in US patent application publication no. 20050255552 and US patent application publication no. 20060134098.

The term "binding specificity determinant" or "BSD" as used in the context of the current invention refers to the minimum contiguous or non-contiguous amino acid sequence within a CDR region necessary for determining the binding specificity of an antibody. In the current invention, the minimum binding specificity determinants reside within a portion or the full-length of the CDR3 sequences of the heavy and light chains of the antibody.

A "human" antibody as used herein encompasses humanized and Humaneered™ antibodies, as well as human monoclonal antibodies that are produced using known techniques.

A "therapeutic" antibody as used herein refers to a human or chimeric antibody that is administered to a patient to treat a disease for which it is desirable to kill eosinophils.

A "hypofucosylated" antibody preparation refers to an antibody preparation in which less than 50% of the N-linked oligosaccharide chains contain α1,6-fucose attached to the CH2 domain. Typically, less than about 40%, less than about 30%, less than about 20%, less than about 10%, or less than 5% or less than 1% of the N-linked oligosaccharide chains contain α1,6-fucose attached to the CH2 domain in a "hypofucosylated" antibody preparation.

The terms "afucosylated" and "non-fucosylated" are used interchangeably herein to refer to an antibody that lacks α1,6-fucose in the carbohydrate attached to the CH2 domain of the IgG heavy chain.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

An "EMR1-dependent disease", as used herein, refers to a disease in which a cell that expresses EMR1 is a target for therapy to treat the disease.

As used herein, "therapeutic agent" refers to an agent that when administered to a patient suffering from a disease, in a therapeutically effective dose, will cure, or at least partially arrest the symptoms of the disease and complications associated with the disease.

The terms "identical" or percent "identity," in the context of two or more polypeptide (or nucleic acid) sequences, refer to two or more sequences or subsequences that are the same or have a specified percentage of amino acid residues (or nucleotides) that are the same (e.g., at least 60% identity, preferably at least 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Sequences sharing at least 60% identity are termed "substantially identical". "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein sequence.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

An indication that two polypeptides are substantially identical is that the first polypeptide is immunologically cross-reactive with the antibodies raised against the second polypeptide. Thus, a polypeptide is typically substantially identical to a second polypeptide, e.g., where the two peptides differ only by conservative substitutions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used in this specification and the appended claims, the singular forms "a," "an," and "the" include plural referents unless the context clearly dictates otherwise.

I. Introduction

The invention relates to antibodies that bind to EMR1 with high affinity and preferably, to antibodies that selectively bind to EMR1, e.g., to the ELD-6 domain of EMR1, and are not cross-reactive with other proteins, such as other EGF-TM7 family members. The domain structure of EMR1 is provided in FIG. 2. In some embodiments of the current invention, the antibodies bind to a linear epitope within the region RDIDE-CRQDPSTCGPNSI (SEQ ID NO:30) (amino acid residues 271 through 288 of SEQ ID NO:1), which is present in the ELD-6 domain.

Antibodies of the invention exhibit high affinity binding to EMR1. The affinity of an antibody may be assessed using well known assays to determine binding activity and affinity. Such techniques include ELISA assays as well as binding determinations that employ surface plasmon resonance or interferometry. For example, affinities can be determined by biolayer interferometry using a ForteBio (Mountain View, Calif.) Octet biosensor.

In some embodiments, an antibody of the invention binds to all or a portion of the EMR1 sequence RDIDECRQDP-STCGPNSI (SEQ ID NO:30). In some embodiments, an antibody of the invention competes with the monoclonal antibody 1E7 antibody, i.e., competes with an antibody that has the $V_H$ and $V_L$ regions of the 1E7 antibody (SEQ ID NOs 23 and 24, respectively) for binding to EMR1. In other embodiments an antibody described herein, e.g., a different antibody comprising a $V_H$ and $V_L$ region combination as shown in the table provided in FIG. 1, can be used as a reference antibody for assessing whether another antibody competes for binding to EMR1. A test antibody is considered to competitively inhibit binding of a reference antibody, if binding of the reference antibody to the antigen is reduced by at least 30%, usually at least about 40%, 50%, 60% or 75%, and often by at least about 90%, in the presence of the test antibody. Many assays can be employed to assess binding, including ELISA, as well as other assays known in the art, such as immunoblots.

In another aspect, the invention provides a method of depleting eosinophils, the method comprising administering an anti-EMR1 antibody to a subject in need of depletion of eosinophils. In some embodiments, the antibody specifically binds EMR1 and is afucosylated. In some embodiments, the antibody preparation that is administered is hypofucosylated. In some embodiments, the anti-EMR1 antibody binds to the ELD-6 domain of EMR1. In some embodiments, the antibody binds to a linear epitope within the region RDIDE-CRQDPSTCGPNSI (SEQ ID NO:30).

Antibodies of the invention comprise variable regions with a high degree of amino acid sequence identity to human germ-line $V_H$ and $V_L$ sequences.

Typically, the portion of the CDR3 excluding the BSD and the complete FR4 are comprised of human germ-line sequences. In some embodiments, the CDR3-FR4 sequence excluding the BSD differs from human germ-line sequences by not more than 2 amino acids on each chain. In some embodiments, the CDR3-FR4 sequence excluding the BSD differs from human germ-line sequences by no more than 1 amino acid on each chain. In some embodiments, the J-segment comprises a human germline J-segment. Human germline sequences can be determined, for example, through the publicly available international ImMunoGeneTics database (IMGT) and V-base (on the worldwide web at vbase.mrc-cpe.cam.ac.uk).

The human germline V-segment repertoire consists of 51 heavy chain V-regions, 40 κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database, provided by the MRC Centre for Protein Engineering, Cambridge, United Kingdom (see, also Chothia et al., 1992, J Mol Biol 227:776-798; Tomlinson et al., 1995, EMBO J. 14:4628-4638; and Williams et al., 1996, J Mol Biol 264:220-232).

II. Examples of anti-EMR1 Antibody Heavy Chains

In some embodiments, a heavy chain variable region of an anti-EMR1 antibody of the invention comprises a heavy-chain V-region that comprises the following elements:

1) human heavy-chain V-segment sequences comprising FR1-CDR1-FR2-CDR2-FR3

2) a CDRH3 region comprising the amino acid sequence IYYRGFDX$_1$ (SEQ ID NO:31), wherein X$_1$ is Q, S, K, or V; and 3) a FR4 contributed by a human germ-line J-gene segment.

In some embodiments, a heavy chain variable region CDR3 (CDRH3) of an anti-EMR1 antibody of the invention comprises IYYRGFDQ (SEQ ID NO:39). In some embodiments, a CDRH3 of an antibody of the invention comprises IYYRG-FDS (SEQ ID NO:40). In some embodiments, a CDRH3 of an antibody of the invention comprises IYYRGFDV (SEQ ID NO:41). In some embodiments, a CDRH3 of an antibody of the invention comprises IYYRGFDK (SEQ ID NO:42).

The V-segment typically has at least 85%, 90%, 95%, or greater identity to a human germline V-segment, e.g., a human Vh3 subclass. Thus, in some embodiments, the V-segment has at least 85%, 86%, 87%, 88%, 89%, 90%, 91%, 92%, 93%, 94%, 95%, 96%, 97%, 98%, or 99% or greater, identity to the germ-line segment Vh3 3-33 sequence. In some embodiments, the V-segment differs by no more than 15 residues from Vh3 3-33. In some embodiments, the V-segment of the heavy chain of an antibody of the invention differs by no more than 10 residues in the framework region compared to the V-segment Vh3-33 framework region.

In some embodiments, an antibody of the invention comprises a V-segment that has at least 90% identity, or at least 91%, 92% 93%, 94%, 95%, 96%, 97%, 98%, 99%, or 100% identity to one of the V-segments of the EMR1 antibody $V_H$ regions shown in FIG. 1. In some embodiments, the percent identity is determined relative to the framework region of the V-segment and excludes the CDRs (CDR1 and CDR2) from the percent identity.

The FR4 sequence of an antibody of the invention is provided by a human JH1, JH2, JH3, JH4, JH5 or JH6 gene germline segment, or a sequence that has a high degree of amino-acid sequence identity, e.g., at least 80% or at least 90% identity, or differs at not more than 3, typically at not more than 2, amino acid residues in comparison to the FR4 region of a human germline JH segment, e.g., a human germline JH6 segment. In some embodiments, the J segment is from a human germline JH6 sequence and the FR4 has the sequence WGQGTTVTVSS (SEQ ID NO:43). A human FR4 for a heavy chain is 11 amino acids in length in a native IgG antibody. The region of a J segment that corresponds to the FR4 can be readily determined based on known antibody structure and known FR4 sequences.

In some embodiments, the V-segment of the $V_H$ region of an anti-EMR1 antibody of the invention has a CDR1 and/or CDR2 as shown in FIG. 1. In some embodiments, the antibody has a heavy chain CDR1 (CDRH1) that comprises $X_1FGX_2H$ (SEQ ID NO:33), wherein $X_1$ is D, S, or N; and $X_2$ is M or I. In some embodiments $X_1$ is Q (SEQ ID NO:44). In some embodiments, the CDRH1 has the sequence DFGMH (SEQ ID NO:45), DFGIH (SEQ ID NO:46), SFGMH (SEQ ID NO:47), SFGIH (SEQ ID NO:48), NFGMH (SEQ ID NO:49), or NFGIH (SEQ ID NO:50).

In some embodiments, an anti-EMR1 antibody of the invention has a heavy chain CDR2 (CDRH2) that comprises VIWSGGSTX$_1$YADSVKG (SEQ ID NO:34), wherein X$_1$ is D, N or Y. In some embodiments, the CDRH2 comprises VIWSGGSTDYADSVKG (SEQ ID NO:51). In some embodiments, the CDRH2 comprises VIWSGGSTNYADSVKG (SEQ ID NO:52). In some embodiments, the CDRH2 comprises VIWSGGSTYYADSVKG (SEQ ID NO:53).

In some embodiments, an anti-EMR1 antibody of the invention has a CDRH3 having the amino acid sequence IYYRGFDX$_1$ (SEQ ID NO:31), wherein X$_1$ is Q, S, K, or V; a CDRH1 having the amino acid sequence X$_1$FGX$_2$H (SEQ ID NO:33) wherein X$_1$ is D, S, or N; and X$_2$ is M or I; and a CDRH2 having the amino acid sequence VIWSGGSTX$_1$YADSVKG (SEQ ID NO:34), wherein X$_1$ is D, N, or Y. In some embodiments, an antibody of the invention has a CDRH3 having the amino acid sequence IYYRGFDV (SEQ ID NO:41); a CDRH1 having the amino acid sequence SFGMH (SEQ ID NO:47) or NFGMH (SEQ ID NO:49); and a CDRH2 having the sequence VIWSGGSTYYADSVKG (SEQ ID NO:53). In some embodiments, an antibody of the invention has a CDRH3 having the amino acid sequence IYYRGFDQ (SEQ ID NO:39); a CDRH1 having the amino acid sequence SFGMH (SEQ ID NO:47) or NFGMH (SEQ ID NO:49); and a CDRH2 having the amino acid sequence VIWSGGSTYYADSVKG (SEQ ID NO:53). In some embodiments, an antibody of the invention has a CDRH3 having the amino acid sequence IYYRGFDS (SEQ ID NO:40); a CDRH1 having the amino acid sequence SFGMH (SEQ ID NO:47); and a CDRH2 having the sequence VIWSGGSTDYADSVKG (SEQ ID NO:51). In some embodiments, an antibody of the invention has a CDRH3 having the amino acid sequence IYYRGFDS (SEQ ID NO:40); a CDRH1 having the amino acid sequence NFGMH (SEQ ID NO:49); and a CDRH2 having the sequence VIWSGGSTYYADSVKG (SEQ ID NO:53). In some embodiments, an antibody of the invention has a CDRH3 having the amino acid sequence IYYRGFDS (SEQ ID NO:40); a CDRH1 having the amino acid sequence SFGIH (SEQ ID NO:48); and a CDRH2 having the sequence VIWSGGSTNYADSVKG (SEQ ID NO:52). In some embodiments, an antibody of the invention has a CDRH3 having the amino acid sequence IYYRGFDS (SEQ ID NO:40); a CDRH1 having the amino acid sequence DFGIH (SEQ ID NO:46); and a CDRH2 having the sequence VIWSGGSTDYADSVKG (SEQ ID NO:51).

In some embodiments, an anti-EMR1 antibody of the invention may have a V$_H$ region CDR3 that has the sequence IYYRGFD(Q/V/S/K) (SEQ ID NO:31) and a CDR1 and/or a CDR2 of any of the V$_H$ regions set forth in FIG. 1.

In some embodiments, a V$_H$ region V-segment of an antibody of the invention has a V-segment sequence shown in FIG. 1.

In some embodiments, an antibody of the invention has a V$_H$ region sequence set forth in FIG. 1.

III. Examples of Anti-EMR1 Antibody Light Chains

In some embodiments, a light chain of an anti-EMR1 antibody of the invention comprises at light-chain V-region that comprises the following elements:
1) human light-chain V-segment sequences comprising FR1-CDR1-FR2-CDR2-FR3

2) a CDRL3 region that has the amino acid sequence X$_1$QGX$_2$HX$_3$PLT (SEQ ID NO:35), where X$_1$ is F, V, T, or N; X$_2$ is S, V, G, or T; and X$_3$ is V, L, or P; and
3) a FR4 contributed by a human germ-line J-gene segment.

In some embodiments, a light chain variable region of an anti-EMR1 antibody of the invention has a CDR3 (CDRL3) that comprises X$_1$QGX$_2$HX$_3$PLT (SEQ ID NO:35), where X$_1$ is F, V, T, or N; X$_2$ is S, V, G, or T; and X$_3$ is V, L, or P. In some embodiments, the CDRL3 has the sequence FQGSHVPLT (SEQ ID NO:54), SQGSHVPLT (SEQ ID NO:55), NQGSHVPLT (SEQ ID NO:56), FQGSHTPLT (SEQ ID NO:57), FQGVHVPLT (SEQ ID NO:58), FQSSHVPLT (SEQ ID NO:59), SQGSHVPLT (SEQ ID NO:60), FQGSHPPLT (SEQ ID NO:61), or VQGTHVPLT (SEQ ID NO:62).

The V$_L$ region comprises either a Vlambda or a Vkappa V-segment. Examples of a Vkappa sequence that supports binding in combination with a complementary V$_H$-region is provided in the table in FIG. 1. The Vkappa or V lambda may be of any subclass.

The Vkappa segments may be of any subclass, e.g., a VκII sequence, such as a VκII A3 sub-class. In some embodiments, the segments have at least 80% sequence identity, or at least 85%, 86%, 87%, 88%, 89%, 90%, or 95%, or greater, sequence identity to a human germline Vkappa sequence, e.g., a VκII A3 sequence. In some embodiments, the Vκ segment may differ by not more than 10 or not more than 5 framework residues relative to the framework regions of VκII A3 In other embodiments, the V$_L$ region V-segment of an antibody of the invention has at least 85% identity, or at least 90%, 91%, 92%, 93%, 94%, 95%, 96%, 97%, 98%, 99%, or 100% identity to the light chain V-segment sequence of an EMR1 V$_L$ region shown in FIG. 1. In some embodiments, the percent identity is to the framework region of the V-segment and excludes the CDRs.

The FR4 sequence of the V$_L$ region of an antibody of the invention is provided by a human germline J segment, e.g. or a sequence that has a high degree of amino-acid sequence identity, e.g., at least 80% or at least 90% identity, to the FR4 region of a human germline J segment, or differs at not more than 3, or not more than 2, amino acids from a human germ-line FR4 region. In some embodiments, the J segment is a human germline J kappa 5 sequence. In some embodiments, the FR4 of the antibody has the sequence FGQGTREIK (SEQ ID NO:63). The human FR4 for a light chain is 10 amino acids in length in a native IgG antibody. The region of a J segment that corresponds to the FR4 can be readily determined based on known antibody structure and known FR4 sequences.

In some embodiments, a light chain variable region of an anti-EMR1 antibody of the invention has a CDRL3 as set forth in FIG. 1 and a CDR1 (CDRL1) having the amino acid sequence X$_1$SSQSX$_2$X$_3$HSNGX$_4$X$_5$YLE (SEQ ID NO:37), wherein X$_1$ is R or K; X$_2$ is L or I; X$_3$ is V or L; X$_4$ is N or Y; and X$_5$ is N or T. In some embodiments, the CDRL1 has the sequence RSSQSIVHSNGNNYLE (SEQ ID NO:64), KSSQSIVHSNGNNYLE (SEQ ID NO:65), RSSQSLVHSNGNNYLE (SEQ ID NO:66), KSSQSLVHSNGNNYLE (SEQ ID NO:67), RSSQSLVHSNGYTYLE (SEQ ID NO:68), RSSQSLVHSNGNTYLE (SEQ ID NO:69), RSSQSLVHSNGYNYLE (SEQ ID NO:70), KSSQSLVHSNGYTYLE (SEQ ID NO:71), KSSQSLVHSNGYTYLE (SEQ ID NO:72), KSSQSLVHSNGNTYLE (SEQ ID NO:73), KSSQSLVHSNGYNYLE (SEQ ID NO:74), KSSQSLVHSNGYTYLE (SEQ ID NO:75), KSSQSILHSNGYTYLE (SEQ ID NO:76), or KSSQSLLHSNGYTYLE (SEQ ID NO:77). In some embodiments, a light chain variable region of an anti-EMR1 antibody of the invention has CDRL3 as set forth in FIG. 1 and a CDR2 (CDRL2) that comprises the amino acid sequence RX$_1$SNRAS (SEQ ID NO:38), wherein X$_1$ is V or G. In some embodiments X$_1$ is V (SEQ ID NO:78). In some embodiments X$_1$ is G (SEQ ID NO:79).

In some embodiments, the V-segment of the V$_L$ region has a CDR1 and/or CDR2 as shown in FIG. 1. Thus, an antibody of the invention may have a CDR1 sequence of RSSQSIVHSNGNNYLE (SEQ ID NO:64), KSSQSIVHSNGNNYLE (SEQ ID NO:65), RSSQSLVHSNGNNYLE (SEQ ID NO:66), KSSQSLVHSNGNNYLE (SEQ ID NO:67), RSSQSLVHSNGYTYLE (SEQ ID NO:68), RSSQSLVHSNGNTYLE (SEQ ID NO:69), RSSQSLVHSNGYNYLE (SEQ ID NO:70), KSSQSLVHSNGYTYLE (SEQ ID NO:71), KSSQSLVHSNGYTYLE (SEQ ID NO:72), KSSQSLVHSNGNTYLE (SEQ ID NO:73), KSSQSLVHSNGYNYLE (SEQ ID NO:74), KSSQSLVHSNGYTYLE (SEQ ID NO:75), KSSQSILHSNGYTYLE (SEQ ID NO:76), or KSSQSLLHSNGYTYLE (SEQ ID NO:77); and/or a CDR2 having the amino acid sequence RVSNRAS (SEQ ID NO:78) or RGSNRAS (SEQ ID NO:79).

In particular embodiments, an anti-EMR1 antibody of the invention may have a V$_L$ region CDR1 and a CDR2 in a combination as shown in one of the V-segments of the V$_L$ regions set forth in FIG. 1 and a V$_L$ region CDR3 sequence that comprises FQGSHVPLT (SEQ ID NO:54), SQGSHVPLT (SEQ ID NO:55), NQGSHVPLT (SEQ ID NO:56), FQGSHTPLT (SEQ ID NO:57), FQGVHVPLT (SEQ ID NO:58), FQSSHVPLT (SEQ ID NO:59), SQGSHVPLT (SEQ ID NO:60), FQGSHPPLT (SEQ ID NO:61), or VQGTHVPLT (SEQ ID NO:62). In some embodiments, such an anti-EphA3 antibody may comprise a V$_L$ region FR4 region that is FGQGTRLEIK (SEQ ID NO:80).

In some embodiments, a V$_L$ region V-segment of an antibody of the invention has a V-segment sequence shown in FIG. 1.

In typical embodiment, an antibody of the invention has a V$_L$ region sequence set forth in FIG. 1.

Examples of Anti-EMR1 Antibodies

In some embodiments, an anti-EMR1 antibody of the invention has a CDRL3 having the amino acid sequence X$_1$QGX$_2$HX$_3$PLT (SEQ ID NO:35), where X$_1$ is F, V, T, or N; X$_2$ is S, V, G, or T; and X$_3$ is V, L, or P; a CDRL1 having the amino acid sequence X$_1$SSQSX$_2$X$_3$HSNGX$_4$X$_5$YLE (SEQ ID NO:37), wherein X$_1$ is R or K; X$_2$ is L or I; X$_3$ is V or L; X$_4$ is N or Y; and X$_5$ is N or T; and a CDRL2 having the amino acid sequence RX$_1$SNRAS (SEQ ID NO:38), wherein X$_1$ is V or G. In some embodiments, such an antibody may have a CDRH3 having the amino acid sequence IYYRGFDX$_1$ (SEQ ID NO:31), wherein X$_1$ is Q, S, K, or V; a CDRH1 having the amino acid sequence X$_1$FGX$_2$H (SEQ ID NO:33), wherein X$_1$ is D, S, or N; and X$_2$ is M or I; and a CDRH2 having the amino acid sequence VIWSGGSTX$_1$YADSVKG (SEQ ID NO:34), wherein X$_1$ is D, N or Y.

In some embodiments, an antibody of the invention has a CDRH3 having the amino acid sequence IYYRGFDX$_1$ (SEQ ID NO:31), wherein X$_1$ is Q, S, K, or V; and a CDRL3 having the amino acid sequence X$_1$QGX$_2$HX$_3$PLT (SEQ ID NO:35), where X$_1$ is F, V, T, or N; X$_2$ is S, V, G, or T; and X$_3$ is V, L, or P. In some embodiments, an antibody of the invention has a CDRH3 having the amino acid sequence IYYRGFDS (SEQ ID NO:40) and a CDRL3 having the amino acid sequence FQGSHVPLT (SEQ ID NO:54). In some embodiments, an antibody of the invention has a CDRH3 having the amino acid sequence IYYRGFDQ (SEQ ID NO:39) and a CDRL3 having the amino acid sequence FQGSHVPLT (SEQ ID NO:54). In some embodiments, an antibody of the invention has a CDRH3 having the amino acid sequence IYYRGFDV (SEQ ID NO:41) and a CDRL3 having the amino acid sequence FQGSHVPLT (SEQ ID NO:54). In some embodiments, an antibody of the invention has a CDRH3 having the amino acid sequence IYYRGFDK (SEQ ID NO:42) and a CDRL3 having the amino acid sequence FQGSHVPLT (SEQ ID NO:54). In some embodiments, an antibody of the invention has a CDRH3 having the amino acid sequence IYYRGFDQ (SEQ ID NO:39) and a CDRL3 having the amino acid sequence FQGSHPPLT (SEQ ID NO:61). In some embodiments, an antibody of the invention has a CDRH3 having the amino acid sequence IYYRGFDV (SEQ ID NO:41) and a CDRL3 having the amino acid sequence FQGSHPPLT (SEQ ID NO:61). In some embodiments, an antibody of the invention has a CDRH3 having the amino acid sequence IYYRGFDV (SEQ ID NO:41) and a CDRL3 having the amino acid sequence SQGSHVPLT (SEQ ID NO:55). In some embodiments, an antibody of the invention has a CDRH3 having the amino acid sequence IYYRGFDQ (SEQ ID NO:39) and a CDRL3 having the amino acid sequence SQGSHVPLT (SEQ ID NO:55). In some embodiments, an antibody of the invention has a CDRH3 having the amino acid sequence IYYRGFDQ (SEQ ID NO:39) and a CDRL3 having the amino acid sequence VQGTHVPLT (SEQ ID NO:62). In some embodiments, an antibody of the invention has a CDRH3 having the amino acid sequence IYYRGFDV (SEQ ID NO:41) and a CDRL3 having the amino acid sequence VQGTHVPLT (SEQ ID NO:62). In some embodiments, an antibody of the invention has a CDRH3 having the amino acid sequence IYYRGFDQ (SEQ ID NO:39) and a CDRL3 having the amino acid sequence NQGTHVPLT (SEQ ID NO:81). In some embodiments, an antibody of the invention has a CDRH3 having the amino acid sequence IYYRGFDV (SEQ ID NO:41) and a CDRL3 having the amino acid sequence NQGTHVPLT (SEQ ID NO:81).

In some embodiments, an anti-EMR1 antibody of the invention has the CDR1, CDR2, and CDR3 of one of the heavy chains in FIG. 1 and the CDR1, CDR2, and a CDR3 of one of the light chains shown in FIG. 1. In some embodiments, the antibody has the heavy chain CDR1, CDR2, and CDR3 of SEQ ID NO:8 and the light chain CDR1, CDR2, and CDR3 of SEQ ID NO:17. In some embodiments, the antibody has the heavy chain CDR1, CDR2, and CDR3 of SEQ ID NO:4 and the light chain CDR1, CDR2, and CDR3 of SEQ ID NO:17. In some embodiments, the antibody has the heavy chain CDR1, CDR2, and CDR3 of SEQ ID NO:9 and the light chain CDR1, CDR2, and CDR3 of SEQ ID NO:17. In some embodiments, the antibody has the heavy chain CDR1, CDR2, and CDR3 of SEQ ID NO:9 and the light chain CDR1, CDR2, and CDR3 of SEQ ID NO:18. In some embodiments, the antibody has the heavy chain CDR1, CDR2, and CDR3 of SEQ ID NO:6 and the light chain CDR1, CDR2, and CDR3 of SEQ ID NO:15. In some embodiments, the antibody has the heavy chain CDR1, CDR2, and CDR3 of SEQ ID NO:7 and the light chain CDR1, CDR2, and CDR3 of SEQ ID NO:16. In some embodiments, the antibody has the heavy chain CDR1, CDR2, and CDR3 of SEQ ID NO:11 and the light chain CDR1, CDR2, and CDR3 of SEQ ID NO:21. In some embodiments, the antibody has the heavy chain CDR1, CDR2, and CDR3 of SEQ ID NO:11 and the light chain CDR1, CDR2, and CDR3 of SEQ ID NO:22. In some embodiments, the antibody has the heavy chain CDR1, CDR2, and CDR3 of SEQ ID NO:9 and the light chain CDR1, CDR2, and CDR3 of SEQ ID NO:21. In some embodiments, the antibody has the heavy chain CDR1, CDR2, and CDR3 of SEQ ID NO:11 and the light chain CDR1, CDR2, and CDR3 of SEQ ID NO:17.

In some embodiments, an anti-EMR1 antibody of the invention has a $V_H$ region and a $V_L$ region that comprise the following pairs of sequences: SEQ ID NO:23 and SEQ ID NO:24; SEQ ID NO:8 and SEQ ID NO:17; SEQ ID NO:4 and SEQ ID NO:17; SEQ ID NO:9 and SEQ ID NO:17; SEQ ID NO:9 and SEQ ID NO:18; SEQ ID NO:6 and SEQ ID NO:15; SEQ ID NO:7 and SEQ ID NO:16; SEQ ID NO:11 and SEQ ID NO:21; SEQ ID NO:11 and SEQ ID NO:22; SEQ ID NO:9 and SEQ ID NO:21; or SEQ ID NO:11 and SEQ ID NO:17.

IV. Preparation of Anti-EMR1 Antibodies

The anti-EMR1 antibodies of the present invention can be produced by any means known in the art, including but not limited to, recombinant expression, chemical synthesis, and enzymatic digestion of antibody tetramers. Full-length monoclonal antibodies can be obtained e.g., by hybridoma or recombinant production. Recombinant expression can be from any appropriate host cells known in the art, for example, mammalian host cells, bacterial host cells, yeast host cells, insect host cells, etc.

Methods for the isolation of antibodies with V-region sequences close to human germ-line sequences have previously been described (US patent application publication nos. 20050255552 and 20060134098). Antibody libraries may be expressed in a suitable host cell including mammalian cells, yeast cells or prokaryotic cells. For expression in some cell systems, a signal peptide can be introduced at the N-terminus to direct secretion to the extracellular medium. Antibodies may be secreted from bacterial cells such as *E. coli* with or without a signal peptide. Methods for signal-less secretion of antibody fragments from *E. coli* are described in US patent application 20070020685.

In some embodiments, to generate an EMR1-binding antibody of the invention, a $V_H$-region as described herein e.g., shown in FIG. 1, is combined with one of the $V_L$-regions as described herein, e.g., shown in FIG. 1, and expressed in any of a number of formats in a suitable expression system. Thus the antibody may be expressed as a scFv, Fab, Fab' (containing an immunoglobulin hinge sequence), F(ab')$_2$, (formed by di-sulfide bond formation between the hinge sequences of two Fab' molecules), whole immunoglobulin or truncated immunoglobulin or as a fusion protein in a prokaryotic or eukaryotic host cell, either inside the host cell or by secretion. A methionine residue may optionally be present at the N-terminus, for example, in polypeptides produced in signal-less expression systems.

Antibodies may be produced using any number of expression systems, including both prokaryotic and eukaryotic expression systems. In some embodiments, the expression system is a mammalian cell expression, such as a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a discistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention may be produced in any number of formats, including as a Fab, a Fab', a F(ab')$_2$, a scFv, or a dAB. An antibody of the invention can also include a human constant region. The constant region of the light chain may be a human kappa or lambda constant region. The heavy chain constant region is often a gamma chain constant region, for example, a gamma-1, gamma-2, gamma-3, or gamma-4 constant region. In other embodiments, the antibody may be an IgA or IgM.

In some embodiments of the invention, the antibody $V_L$ region, e.g., a $V_L$ region set forth in FIG. 1, is combined with a human kappa constant region to form the complete light-chain.

In some embodiments of the invention, the $V_H$ region is combined a human gamma constant regions, e.g., a human gamma-1 constant region. Any suitable gamma-1 allotype can be chosen.

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, the antibodies of the invention are in the form of a Fab' or a F(ab')$_2$.

A full-length light chain is generated by fusion of a $V_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd' fragment generated by fusion of a $V_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. The Fab' antibodies of the invention may also be hybrid sequences, e.g., a hinge sequence may be from one immunoglobulin sub-class and the CH1 domain may be from a different sub-class.

An antibody that is employed in the invention can be in numerous formats. In some embodiments, the antibody can include an Fc region, e.g., a human Fc region. For example, such antibodies include IgG antibodies that bind EMR1 and that have an active isotype. In some embodiments, the antibody can be a binding fragment, such as an Fab, Fab', F(ab')$_2$, Fv, scFv, or a single domain antibody ("dAb"). For example, in some embodiments, the antibody may be a F(ab')$_2$. Other exemplary embodiments of antibodies that can be employed in the invention include activating nanobodies or activating camelid antibodies. Such antibodies may additionally be recombinantly engineered by methods well known to persons of skill in the art. As noted above, such antibodies can be produced using known techniques. As appreciated by one of skill in the art, in some embodiments when an antibody is in a format that can be monovalent, e.g., an Fv or Fab format, the antibody may be employed as a multivalent antibody, such as a trivalent or tetravalent antibody. Methods of generating multivalent antibodies re known (see, e.g., King et al., *Cancer Res.* 54:6176-6185, 1994).

In some embodiments, an antibody for use in the invention has an Fc constant region that has an effector function, e.g., binds to an Fc receptor present on immune effector cells. Exemplary "effector functions" include C1q binding; complement-dependent cytotoxicity (CDC); Fc receptor binding; antibody-dependent cell-mediated cytotoxicity (ADCC); phagocytosis; down regulation of cell surface receptors (e.g., B cell receptor), and the like. Such effector functions generally require the Fc region to be combined with a binding domain (e.g. an antibody variable domain) and can be assessed using known assays (see, e.g., the references cited hereinbelow.)

Anti-EMR1 antibodies that have an active isotype and are bound to Fc-receptors on eosinophils can induce cell death by ADCC.

The Fc region can be from a naturally occurring IgG1, or other active isotypes, including IgG3, IgM, IgA, and IgE. "Active isotypes" include antibodies where the Fc region comprises modifications to increase binding to the Fc receptor or otherwise improve the potency of the antibody. Such an Fc constant region may comprise modifications, such as mutations, changes to the level of glycosylation and the like, that increase binding to the Fc receptor. There are many methods of modifying Fc regions that are known in the art. For example, U.S. Patent Application Publication No. 20060039904 describes variants of Fc receptors that have enhanced effector function, including modified binding affinity to one or more Fc ligands (e.g., FcγR, C1q). Additionally, such Fc variants have altered ADCC and/or CDC activity. Other Fc variants include those disclosed by Ghetie et al., *Nat. Biotech.* 15:637-40, 1997; Duncan et al, *Nature* 332:563-564, 1988; Lund et al., *J. Immunol.* 147:2657-2662, 1991; Lund et al, *Mol Immunol* 29:53-59, 1992; Alegre et al, *Transplantation* 57:1537-1543, 1994; Hutchins et al., *Proc Natl. Acad Sci USA* 92:11980-11984, 1995; Jefferis et al, *Immunol Lett.* 44:111-117, 1995; Lund et al., *FASEB J* 9:115-119, 1995; Jefferis et al, *Immunol Lett* 54:101-104, 1996; Lund et al, *J Immunol* 157:4963-4969, 1996; Armour et al., *Eur J Immunol* 29:2613-2624, 1999; Idusogie et al, *J Immunol* 164:4178-4184, 200; Reddy et al, *J Immunol* 164:1925-1933, 2000; Xu et al., *Cell Immunol* 200:16-26, 2000; Idusogie et al, *J Immunol* 166:2571-2575, 2001; Shields et al., *J Biol Chem* 276: 6591-6604, 2001; Jefferis et al, *Immunol Lett* 82:57-65. 2002; Presta et al., *Biochem Soc Trans* 30:487-490, 2002; Lazar et al., *Proc. Natl. Acad. Sci. USA* 103:4005-4010, 2006; U.S. Pat. Nos. 5,624,821; 5,885,573; 5,677,425; 6,165,745; 6,277, 375; 5,869,046; 6,121,022; 5,624,821; 5,648,260; 6,194,551; 6,737,056; 6,821,505; 6,277,375; 7,335,742; and 7,317,091; and PCT Publications WO 94/2935; WO 99/58572; WO 00/42072; WO 02/060919, and WO 04/029207.

Glycosylation is a form of post-translational modification by which carbohydrates (sugars) are enzymatically linked to macromolecules to produce glycans. In the context of the present invention, carbohydrates are typically attached to antibody Fc region via one or more N-linkages (through a nitrogen of asparagine or arginine side chains); however, O-linkages (via hydroxy oxygen of serine, threonine, tyrosine, hydroxylysine, or hydroxyproline side chains) are also possible. Generally, IgG antibodies have a conserved N-linked glycosylation site in the CH2 domain at residue Asn297, while some classes and subclasses also have O-linked sugars, often in the hinge region, e.g. IgD and IgA of some species. The sugars are typically complex, high-mannose, branched sugars; in the case of N-linkages, the sugar that attaches directly to the amino acid sidechain nitrogen is typically N-acetyl glucosamine.

In some embodiments, the glycosylation of Fc regions may be modified. For example, a modification may be aglycosylation, for example, by altering one or more sites of glycosylation within the antibody sequence. Such an approach is described in further detail in U.S. Pat. Nos. 5,714,350 and 6,350,861. An Fc region can also be made that has an altered type of glycosylation, such as a hypofucosylated Fc variant having reduced amounts of fucosyl residues, or an afucosylated Fc variant lacking fucosyl residues, or an Fc variant having increased bisecting GlcNAc structures. Such carbohydrate modifications can be accomplished by, for example, expressing the antibody in a host cell with altered glycosylation machinery. Cells with altered glycosylation machinery, including rat myeloma cells as well as yeast and plants, have been described in the art and can be used as host cells in which to express recombinant antibodies of the invention to thereby produce an antibody with altered glycosylation.

Umana et al, *Nat. Biotechnol* 17:176-180, 1999, which describes bisected GlcNac resulting in 10 times ADCC. Umana notes that such bisected molecules result in less fucosylation. Davies, et al., *Biotechnol. Bioeng.* 74:288-294, 2001 describe CHO cells with inserted enzyme β1-4-N-acetylglucosaminyltransferase III (GnTIII) (which causes the bisected GlcNac structure) resulting in increased ADCC of anti-CD20 antibodies. (Umana) U.S. Pat. No. 6,602,684 describes cells engineered to produce bisecting GlcNac glycoproteins.

Examples of methods to reduce fucosylation of an antibody preparation are provided in Shields et al, *J Biol Chem* 277:26733-26740, 2002, which describes CHO cells (Lec13) deficient in fucosylation to produce IgG1 and further describes that binding of the fucose-deficient IgG1 to human FcgammaRIIIA was improved up to 50-fold and increased ADCC. In addition, Shinkawa et al., *J Biol Chem* 278:3466-3473, 2003; compare IgG produced in YB2/0 and CHO cells. The YB2/0 cells have decreased fucosylation and increased bisecting GlcNac content. Niwa et al., *Clinc. Cancer Res.* 1-:6248-6255, 2004 compare anti-CD20 antibodies with antibodies made in YB2/0 cells (low fucosylation) and observed enhanced ADCC in the latter. Examples of techniques to produce afucosylated antibodies are provided, for example, in Kanda et al, *Glycobiology* 17:104-118, 2006. U.S. Pat. No. 6,946,292 (Kanda) describes fucosyltransferase knock-out cells to produce afucosylated antibodies. U.S. Pat. No. 7,214, 775 and WO 00/61739 describe antibody preparations in which 100% of the antibodies are afucosylated.

Other techniques to modify glycosyation are also known. See, for example, U.S. Patent Application Publication Nos. 20070248600; 20070178551 (GlycoFi technology methods employing engineered lower eukaryotic cells (yeast) to produce "human" glycosylation structures); 20080060092 (Biolex technology methods employing engineered plants to produce "human" glycosylation structures); 20060253928 (which also described engineering of plants to produce "human" antibodies.

Additional techniques for reducing fucose include ProBioGen technology (von Horsten et al., *Glycobiology*, (advance access publication Jul. 23, 2010); Potelligent™ technology (Biowa, Inc. Princeton, N.J.); and GlycoMAb™ glycosylation engineering technology (GLYCART biotechnology AG, Zurich, Switzerland).

The N-linked oligosaccharide content of an antibody can be analyzed by methods known in the art. The following is an example of such a method: Antibodies are subjected to digestion with the enzyme N-glycosidase F (Roche; TaKaRa). Released carbohydrates are analyzed by matrix assisted laser desorption/ionization time-of-flight mass spectrometry (MALDI-TOF MS) with positive ion mode (Papac et al., *Glycobiol.* 8: 445-454, 1998). Monosaccharide composition is then characterized by modified high-performance anion exchange chromatography (HPAEC) (Shinkawa et al., *J. Biol. Chem.* 278: 3466-3473, 2003).

In some embodiments of the invention, the antibody is additionally engineered to reduce immunogenicity, e.g., so that the antibody is suitable for repeat administration. Methods for generating antibodies with reduced immunogenicity include humanization and humaneering procedures and modification techniques such as de-immunization, in which an antibody is further engineered, e.g., in one or more framework regions, to remove T cell epitopes.

V. Administration of Anti-EMR1 Antibodies for the Treatment of Diseases in which EMR1 is a Target The invention also provides methods of treating a patient that has a disease in which it is desirable to kill EMR1-expressing cells, e.g., eosoniphils, by administering an anti-EMR1 antibody. In some embodiments, the patient has an allergic and/or atopic response associated with eosinophilia, such as, but not limited to, chronic obstructive pulmonary disease, chronic eosinophilic pneumonia, asthma, including allergic asthma, allergic bronchopulmonary aspergillosis, allergic colitis, inflammatory bowel disease, coeliac disease, gastroesophageal reflux disease, nasal polyposis, eosinophilic gastroenteritis, eosinophilic gastritis, eosinophilic esophagitis, eosinophilic colitis, Churg-Strauss syndrome, eosinophilic myalgia syndrome, hypereosinophilic syndrome, episodic angioedema, onchocercal dermatitis, atopic dermatitis, eczema, an eosinophilic pulmonary disease that results from helminthic infections, eosinophilic panniculitis, episodic angioedema with eosinophilia (Gleich syndrome), acute eosinophilic interstitial nephritis and renal failure with bone marrow-lymph node granulomas and anterior uveitis, Samter's syndrome, bronchial asthma, intolerance to aspirin, chronic rhinosinusitis, NARES (nonallergic rhinitis with eosinophilia syndrome), drug or toxin-induced pneumonitis, or acute or chronic eosinophilic leukemia. In some embodiments, the patient has chronic obstructive pulmonary disease. In some embodiments an anti-EMR1 antibody of the invention is administered to a subject after nasal polyp removal to prevent or reduce the recurrence of polyps.

The methods of the invention comprise administering an anti-EMR1 antibody as a pharmaceutical composition to a patient in a therapeutically effective amount using a dosing regimen suitable for treatment of the disease. The composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy*, 21st Edition, Philadelphia, Pa. Lippincott Williams & Wilkins, 2005.

The anti-EMR1 antibody is provided in a solution suitable for injection into the patient such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxillary pharmaceutical substances as required to approximate physiological conditions, such as pH adjusting and buffering agents, tonicity adjusting agents, and the like.

The pharmaceutical compositions of the invention are administered to a patient that has an eosinophil-mediated disease, e.g., a patient that has allergic asthma or chronic obstructive pulmonary disease, in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose include amelioration of symptoms of the disease in the patient. Amounts effective for this use will depend upon the severity of the disease and the general state of the patient's health, including other factors such as age, weight, gender, administration route, etc. Single or multiple administrations of the antibody may be administered depending on the dosage and frequency as required and tolerated by the patient. In any event, the methods provide a sufficient quantity of anti-EMR1 antibody to effectively treat the patient.

The antibody can be administered by injection or infusion through any suitable route including but not limited to intravenous, sub-cutaneous, intramuscular or intraperitoneal routes. In some embodiments, the antibody may be administered by insufflation. In an exemplary embodiment, the antibody may be stored at 10 mg/ml in sterile isotonic aqueous saline solution for injection at 4° C. and is diluted in either 100 ml or 200 ml 0.9% sodium chloride for injection prior to administration to the patient. In some embodiments, the antibody is administered by intravenous infusion over the course of 1 hour at a dose of between 0.01 and 25 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.01 mg/kg body weight to about 25 mg/kg body weight or in the range 1 mg-2 g per patient. Preferably the dose is in the range 0.1-10 mg/kg or approximately 50 mg-1000 mg/patient. The dose may be repeated at an appropriate frequency which may be in the range once per day to once every three months, or every six months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months or once every 6 months. In other embodiments, the antibody is administered approximately once per month.

An anti-EMR1 antibody of the invention that depletes eosinophils may be administered with one or more additional therapeutic agents, e.g., an agents that decreases inflammation, such as a corticosteroid; an IL-5 blocking agent; a non-steroidal anti-inflammatory drug, and other known agents.

VI. Diagnostic and Prognostic Methods

An anti-EMR1 antibody may also be used for diagnostic and prognostic purposes. Such antibodies include, but are not limited to, a mouse monoclonal antibody such as 19-4G9, 18-2G11, or 4262-5 (see, Table 1); an antibody that selectively binds to ELD-6 of EMR1; or an antibody that has a $V_H$ region and/or $V_L$ region as described herein. For example, the $V_H$ and/or $V_L$ region may be used for clinical analysis, such as detection of EMR1 levels on cells from a patient. A $V_H$ or $V_L$ region of the invention may also be used, e.g., to produce anti-Id antibodies.

In some embodiments, a subject may be evaluated to determine if the subject is a candidate for treatment with an agent, such as an anti-EMR1 antibody of the invention, that selectively depletes eosinophils. A biological sample from the subject is evaluated for the presence of eosinophils in a tissue of interest and/or peripheral blood. For example, if the patient has asthma or eosiniphilic pulmonary disease, sputum or a lavage sample may be analyzed. Patients that have, or are suspected of having, an eosinophilic gastroinflammatory disorder may undergo biopsy such that the inflamed gastrointestinal tissue can be evaluated. In other embodiments, a blood sample may be evaluated for the presence of levels of eosinophils above normal.

In some embodiments, IL-5 receptor (IL-5R) may be evaluated to identify a patient that is a candidate for treatment with an anti-EMR1 antibody that selectively depletes eosinophils, e.g., an antibody that binds to ELD-6 as described herein. IL-5R is expressed on eosinophils and basophils (see, e.g., Miyiajima et al., Blood 82:1960-1974, 1993) and various immunological methods can be employed that use IL-5R antibodies to determine levels of eosinophils in the blood or tissue sample of interest. In some embodiments, the presence of a splice variant of IL-5R that is a soluble IL-5R (sIL-5-R) is associated with eosinophilic disease (Semic-Jusufagic, et al., Pediatr Allergy Immunol. 21:1052-1058, 2010) and may be used to identify a patient that is a candidate for treatment with a therapeutic anti-EMR1 antibody of the invention. The soluble splice variant can be detected by ELISA or by using methods to detect sIL5r RNA, e.g., RT-PCR (Perez et al., BMC Biotechnology 3:17, 2003).

A patient that has an inflammatory or allergic disease and that has elevated eosinophils may be treated with an anti-EMR1 antibody of the invention. In the context of this invention, a patient has elevated eosinophils when the level in a blood sample is above normal or when a tissue sample is shown to have a level of eosinophils infiltration above normal. The normal level may be determined in a patient that does not have an eosinophilic disease.

EXAMPLES

Example 1

Identification of EMR1-Specific Monoclonal Antibodies

Splenic B cells from mice immunized with purified human EMR1-Fc fusion protein were fused with SP2/0-Ag14 cells to generate hybridoma cell lines. Supernatants containing antibody from monoclonal lines were tested for binding to recombinant human EMR1 by ELISA. Antibodies that bound EMR1 were tested for binding to human eosinophils by flow cytometry. Polymorphonuclear-cell rich fractions from buffy coat blood were obtained by Ficoll gradient centrifugation and residual red blood cells were lysed with ammonium chloride (ACK lysis buffer). Eosinophils were isolated by negative selection using a MACS eosinophil isolation kit (Miltenyi) and incubated with 10 µg/ml rat IgG and 2% BSA to block nonspecific IgG binding before addition of anti-EMR1 antibody or isotype control antibody. Anti-mouse FITC antibody was used for detection of bound antibodies on a FACSCalibur flow cytometer.

Binding of anti-EMR1 antibodies to other peripheral blood cell types was analyzed by flow cytometry as follows. Peripheral blood mononuclear cell fractions (PBMC) were isolated from buffy coat preparations by Ficoll density centrifugation, treated with 10 µg/ml rat IgG and 2% BSA to block nonspecific binding followed by anti-EMR1 antibody at 5 µg/ml. After washing, cells were incubated with anti-mouse phycoerythrin, washed and separate samples were incubated with anti-CD3-FITC to detect T cells, anti-CD20-FITC to detect B cells, anti-CD56-FITC to detect NK cells, anti-CD14-FITC to detect monocytes, anti-IgE receptor-FITC to detect basophils or anti-CD16-FITC to detect neutrophils from the granulocytic (high side-scatter) population. After washing, propidium iodide was added to exclude dead cells from flow cytometric analysis. Antibodies 19-1E7, 19-4G9, 4262-5 and 18-2G11 bound selectively to eosinophils with no detectable binding to lymphocytes, monocytes, neutrophils or basophils (See, Table 1). Four additional anti-EMR1 antibodies bound both eosinophils and monocytes and one of these clones (19-3D2) bound to basophils.

Antibody 19-1E7 and antibody 4262-5 were also tested for binding to macrophages. Isolated PBMC from buffy coat preparations were plated in RPMI 1640 media with 10% FBS, IL3, and GM-CSF for 10 days to induce differentiation of monocytes to macrophages. Adherent macrophages were then harvested, blocked and probed for EMR1 as described above, and anti-CD14-FITC was used to stain macrophages. No binding to adherent CD14+ macrophages was observed.

TABLE 1

Binding of anti-EMR1 monoclonal antibodies to human peripheral blood cells.

| Sample | Human EMR1 | Cyno EMR1 | Eosin | T-Cells | B-Cells | NK Cells | Neut | Mon | Mac | Bas |
|---|---|---|---|---|---|---|---|---|---|---|
| 19-1E7 | + | + | + | − | − | − | − | − | − | − |
| 19-2H7 | + | + | + | − | − | − | − | + | − | − |
| 20-3F1 | + | + | + | − | − | − | − | + | | |
| 19-4G9 | + | − | + | − | − | − | − | − | | − |
| 19-4H10 | + | + | + | − | − | − | − | + | | |
| 4262-5 | + | + | + | − | − | − | − | − | − | − |
| 18-6F3-2B3 | + | + | − | | | | | | | |
| 19-3D2 | + | +/− | + | − | − | − | − | + | | + |
| 18-2G11 | + | − | + | − | − | − | − | − | | − |
| 19-3G9 | + | − | | | | | | | | |

Eosin = Eosinophils,
Neut = Neutrophils,
Mon = Monocytes,
Mac = Macrophages,
Bas = Basophils Example 2

Generation of Chimeric 19-1E7 (c1E7) Antibody

The heavy and light V-regions from murine hybridoma 19-1E7 were cloned by RT-PCR using the primer sets described in Chardes et al., FEBS Letters 452:386-394

(2007). The variable region sequences of the 19-1E7 heavy and light chain variable regions are shown below. CDR sequences are underlined:

```
19-1E7 Vh:                              (SEQ ID NO: 23)
QVQLKESGPGLVAPSQSLSITCTVSGFSLTNFGIHWV

RQPPGKGLEWLGVIWSGGGTNYNSALMSRLSISKDNS

KSQVFLKMNSLQTDDTAIYYCVSIYYRGFDSWGQGTT

LTVSS 19-1E7 Vk:                              (SEQ ID NO: 24)
DVFMTQAPLSLPVSLGDQASISCRSSQSIVHSNGNTY

LEWYLQKPGQSPKLLIYRVSNRFSGVPDRFSGSGSGT

DFTLKISRVEAEDLGVYYCFQGSHVPLTFGAGTRLELK
```

Further PCR was used to amplify the V-heavy and V-kappa regions and incorporate restriction enzyme sites suitable for cloning into expression vectors for expression and secretion from *E. coli*. The V-regions were cloned into an expression vector (and named EMS) and expressed and secreted as Fab fragments in *E. coli*. The EMS Fab bound to EMR1-Fc antigen in an ELISA assay. The 19-1E7 heavy and light variable regions were also combined with human gamma-1 Fc and kappa constant regions in the pEE12.4 mammalian expression vector to generate the chimeric 19-1E7 IgG1k antibody (designated c1E7). The c1E7 expression plasmid was transfected into the CHOK1 SV cell line for production of IgG with carbohydrate containing fucose and into the MS704-PF CHO cell line for production of IgG lacking fucose.

For transfections, 2 µg of pEE12.4 c1E7 DNA was incubated with 6 µl of Fugene HD (Roche 04709691001) in 100 µl of Opti-MEM I medium for 20 minutes at room temperature before being added drop-wise to CHO cells plated at $1.5\times10^6$ cells/well of a 6-well plate and incubated overnight. Transfected cells were then diluted into EX-CELL 325 PF CHO Protein-Free Medium with HT supplement, GS supplement (Sigma 58672C) and 50 µM MSX (Sigma M5379) and 10 mg/L phenol red (Sigma P0290) and plated at 0.2 ml/well in 96-well plates. After initial screening by Western blot (see below), transfected cell lines were expanded and subcultured in EX-CELL 325 PF CHO Protein-Free Medium with HT supplement, GS supplement, and 25 µM MSX. Cells were grown in humidified incubators at 37° C. with 5% $CO_2$. Secreted IgG was purified by Protein A affinity chromatography from CHOK1 SV transfectant clones to prepare fucosylated chimeric 1E7 (c1E7) and from MS704-PF transfectants to prepare non-fucosylated c1E7.

Example 3

Identification of a Linear Epitope Bound by Anti-EMR1 Chimeric Monoconal Antibody 19-1E7

Monoclonal antibody 19-1E7 binds to human and cynomolgus EMR1 and does not bind to CD97 or EMR2. Epitope mapping was performed to identify the binding site on EMR1 to which the antibody binds. Initial Western blot analysis of EMR1 with chimeric 1E7 (c1E7) antibody under reducing conditions suggested that c1E7 binds to a linear epitope on EMR1 that is not affected by reduction and denaturation by boiling in buffer containing SDS. To produce monomeric EMR1, EMR1-Fc was treated with papain and released Fc tag was captured on protein A column. Monomeric EMR1 was further digested with carboxy peptidase Y and generated protein fragments were analyzed by Western blot with c1E7 antibody as shown in FIG. 3. The Western blot analysis indicated that c1E7 did not bind to EMR1 lacking approximately 100 residues at the C-terminal end of the protein. As shown in FIG. 3, c1E7 antibody did not bind to EMR1 deletion mutant that has no ELD-6. To further define the epitope, three overlapping peptides that cover 54 amino acids of ELD-6 were analyzed for binding to c1E7 by biolayer interferometry using a ForteBio Octet instrument. Peptides used to span the ELD-6 positions 268-316 of SEQ ID NO:1 were:

```
Peptide 1:                              (SEQ ID NO: 82)
27 mer: 271RDIDECRQDPSTCGPNSICTNALGSYS297

Peptide 2:                              (SEQ ID NO: 83)
28 mer: 297SCGCIAGFHPNPEGSQKDGNFSCQRVNS324

Peptide 3:                              (SEQ ID NO: 84)
26 mer: 285PNSICTNALGSYSCGCIAGFHPNPEG310
```

Figure 4:
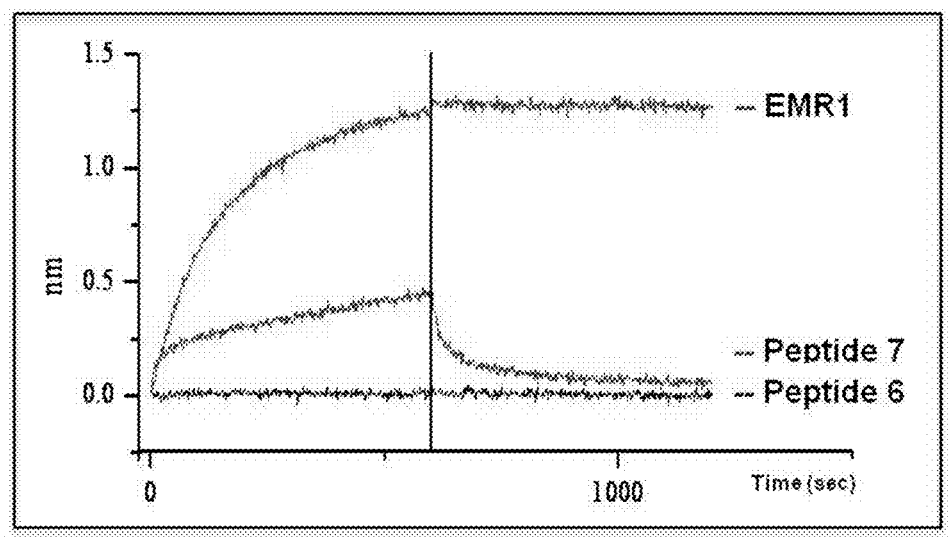
FIG. 4 provides data showing binding of anti-EMR1 monoclonal antibody c1E7 to peptides representing various regions of EMR1 by ForteBio: peptides 6 and 7 in the C-terminal sequence of human EMR1-ELD in the ELD-6 region were tested for binding by c1E7.

The results of the binding analysis are provided in FIG. 4 and show that the antibody binds to peptide 1. Two more peptides (4 and 5) that span peptide 1 were analyzed by ForteBio. Their sequences were:

```
Peptide 4:                              (SEQ ID NO: 85)
20 mer: 271RDIDECRQDPSTCGPNSICT290

Peptide 5:                              (SEQ ID NO: 86)
21 mer: 277RQDPSTCGPNSICTNALGSYS297
```

Biolayer interferometry binding data indicated binding of c1E7 to peptide 4 but not to peptide 5. Two more peptides (6 and 7) that span peptide 4 were analyzed by ForteBio. Their sequences were:

```
Peptide 6:                              (SEQ ID NO: 87)
18 mer: 273IDECRQDPSTCGPNSICT290

Peptide 7:                              (SEQ ID NO: 30)
18 mer: 271RDIDECRQDPSTCGPNSI288
```

ForteBio data shown binding of c1E7 to peptide 7 but not to peptide 6 (FIG. 4). The epitope mapping analysis showed that the c1E7 epitope lies within sequence region:

```
                                        (SEQ ID NO: 30)
        271RDIDECRQDPSTCGPNSI288.
```

TABLE 2

Binding of c1E7 to peptides spanning EMR1 ELD6.
EMR1 ELD-6 positions 271-324
Binding of c1E7 to peptide by ForteBio

| Peptide | Bound | Sequence | (SEQ ID NO:) |
|---|---|---|---|
| 1 | + | $^{271}$RDIDECRQDPSTCGPNSICTNALGSYS$^{297}$ | (82) |
| 2 | – | $^{297}$SCGCIAGFHPNPEGSQKDGNFSCQRVNS$^{324}$ | (83) |
| 3 | – | $^{285}$PNSICTNALGSYSCGCIAGFHPNPEG$^{310}$ | (84) |
| 4 | + | $^{271}$RDIDECRQDPSTCGPNSICT$^{290}$ | (85) |
| 5 | – | $^{277}$RQDPSTCGPNSICTNALGSYS$^{297}$ | (86) |
| 6 | – | $^{273}$IDECRQDPSTCGPNSICT$^{290}$ | (87) |
| 7 | + | $^{271}$RDIDECRQDPSTCGPNS$^{288}$ | (30) |

Example 4

ADCC Activity of Chimeric 1E7 Antibody

Figure 5:
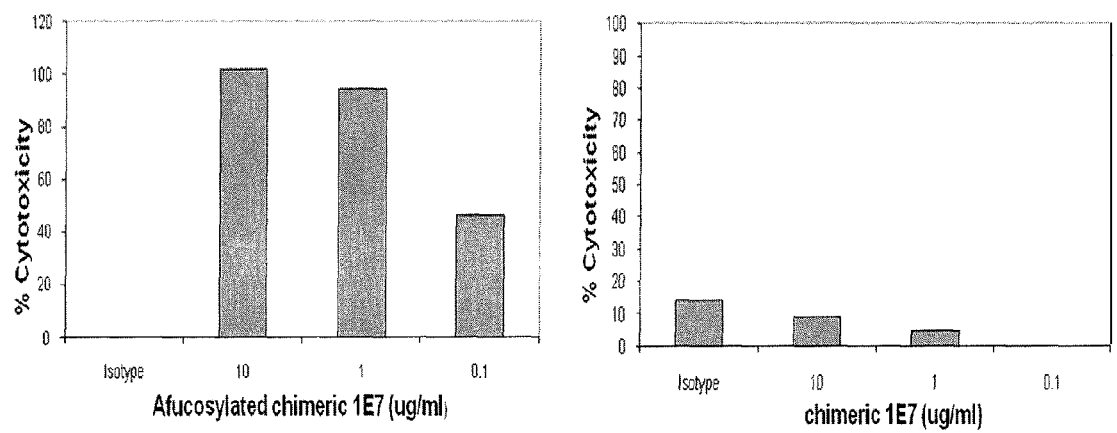
FIG. 5 provides data showing that a nonfucosylated antibody mediates potent ADCC activity. Eosinophils (85,000 cells) and NK cells were combined with antibody, c1E7, at 10 µg/ml, 1 µg/ml and 0.1 µg/ml and analyzed for ADCC activity. A human IgG1 isotype control antibody was assayed at 10 µg/ml. Left panel: nonfucosylated c1E7; right panel fucosylated c1E7.

Anti-EMR1 antibodies were tested for Antibody Dependent Cell-mediated Cytotoxicity (ADCC) activity against eosinophil target cells. Human eosinophils isolated as described in Example 1, were maintained overnight in RPMI 1640 medium with 10% FCS and 0.1 nM IL-5. From the same buffy coat preparation, NK cells were isolated from the PBMC layer of the ficoll gradient and negative selection using an NK cell isolation kit (Miltenyi). Isolated NK cells were grown and expanded overnight in RPMI1640 with 10% FCS and 30 ng/ml IL-2. Eosinophils and NK cells were combined at a 1:1 target to effector-cell ratio and incubated with anti-EMR1 antibody overnight at 37° C. with 5% $CO_2$. ADCC activity was measured by LDH release using a Cytotox 96 Cytotoxicity assay kit (Promega) (FIG. 5).

Nonfucosylated c1E7 showed higher ADCC activity than c1E7 antibody containing fucose. A comparison of nonfucosylated chimeric 1E7 to chimeric 1E7 showed near complete cytotoxicty at 10 μg/ml and 1 μg/ml for nonfucosylated 1E7 and no detectable ADCC activity by the fucosylated antibody at concentrations up to 10 μg/ml.

Example 5

Engineering of 1E7 to Obtain Engineered Antibodies Having V-Region Sequences Highly Homologous to Human Germline Sequences The 1E7 antibody was HUMANEERED™ (engineered to include human sequences). Epitope-focused libraries were constructed from human V-segment library sequences linked to the unique CDR3-FR4 region containing the BSD and human germ-line J-segment sequences. The full-length Vh (Vh3 and Vh4) and Vk (VkII) segment libraries were used as a base for construction of "cassette" libraries in which only part of the murine V-segment is initially replaced by a library of human sequences. Several types of cassette libraries were constructed for both the Vh and Vk chains. Cassettes for the V-heavy and V-kappa chains were made by overlap extension PCR with overlapping common sequences within the framework 2 region. In this way "front-end", "middle", and FR3 human cassette libraries were constructed for both human Vh3 and Vh4 subclasses. "Front end", "middle", and FR3 cassette libraries were constructed for the human Vk II subclass.

Figure 6:
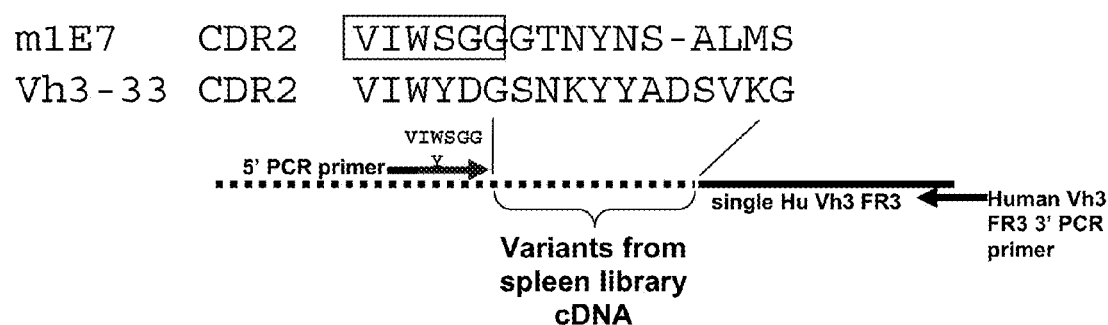
FIG. 6 depicts heavy chain CDR2/FR3 cassette construction for engineering a heavy chain of an anti-EMR1 antibody based on monoclonal antibody 19-1E7 heavy chain variable region (SEQ ID NO:26) sequences. The heavy chain CDR2 of the germ-line Vh3-33 segment (SEQ ID NO:27) is shown for comparison.

Additionally, CDR cassette libraries consisting of engineered CDRs were constructed. In a CDR cassette library, amino acid variation is introduced into a CDR PCR primer and the variants are co-amplified with a library of partial CDR sequences along with a single framework sequence or with a library of framework sequences derived from a human spleen V-segment library. The construction of a heavy chain CDR2 cassette library is illustrated in FIG. 6. The first six residues (along with a Y variant) of the reference CDR2 were retained (boxed) and are encoded by the 5' PCR primer. The 3' PCR primer is complementary to human germ-line Vh3 FR3. The primers were used to amplify and append a single selected human Vh3 FR3 (derived from spleen mRNA) to the engineered CDR2 library. Consecutive overlap extension PCR reactions were used to attach "front end" and CDR3-FR4 cassettes to construct a functional, engineered heavy chain V-region library.

Figure 7:
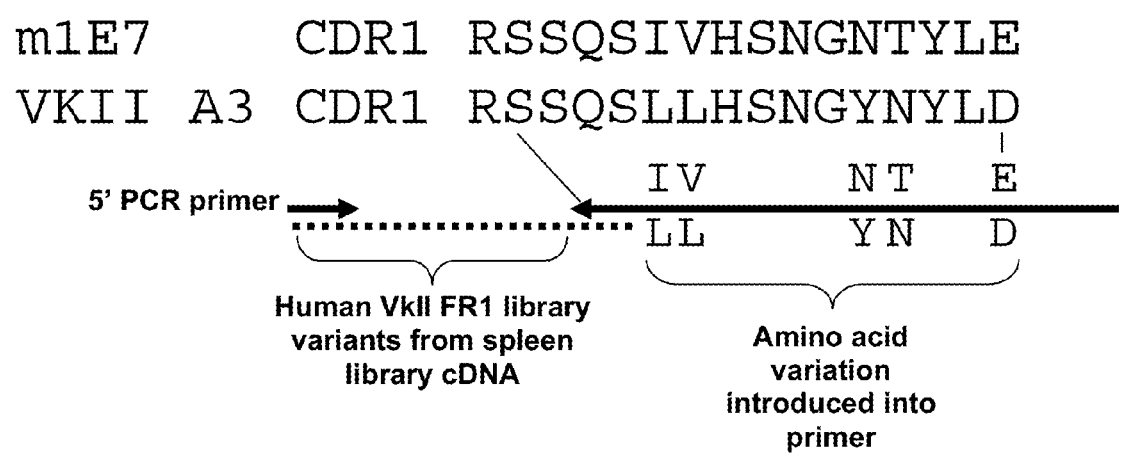
FIG. 7 depicts light chain CDR1/FR1 cassette construction for engineering a light chain of an anti-EMR1 antibody based on monoclonal antibody 19-1E7 light chain variable region (SEQ ID NO:28) sequences. The light chain CDR2 CDR1 of the germ-line VkII A3 segment (SEQ ID NO:29) is shown for comparison.

A second CDR cassette library strategy for the light chain FR1-CDR1 is shown in FIG. 7. A reverse primer coding for amino acid variants at several positions in CDR1 was synthesized. The cassette primer and a forward primer were used to PCR amplify a FR1-CDR1 library from human spleen cDNA. A overlap extension PCR reaction was used to attach the FR1-CDR1 cassette to a FR2-CDR2-CDR3 cassette in order to construct a functional, engineered light chain V-region library.

Human Vheavy and Vkappa cassettes that supported binding to the antigen were identified by a colony-lift binding assay and a rank order was determined according to affinity by ELISA. Colony-lift binding screens of heavy chain variants identified FR1-CDR1, CDR2-FR3 and FR3-CDR3-FR4 cassettes that supported EMR1-Fc recombinant fusion protein antigen binding. Colony-lift binding screens of light chain variants identified FR1-CDR1, "middle" and FR3-CDR3-FR4 cassettes that supported antigen binding. The functional cassettes for each chain were recombined by overlap extension PCR and subsequently screened by a colony-lift binding assay in order to select a fully engineered high affinity Fab that bound antigen.

After the identification of a pool of high affinity, fully engineered Fabs, CDR3 affinity maturation libraries were built. The common CDR3BSD sequences of a panel of engineered Fab clones were mutated using degenerate PCR primers to generate libraries. These mutagenic libraries were screened using colony-lift binding and ELISA assays. The selected Fabs were ranked for affinity by ELISA and ForteBio kinetic analysis. Mutations that supported similar or improved affinity for antigen when compared to the chimeric Fab were identified and are shown in FIG. 8. The heavy chain and light chain CDR3 mutations that support or improve antigen binding help to define the BSD region for each CDR.

Example 6

Depletion of Eosinophils Using an Anti-EMR1 Antibody

Figure 9:
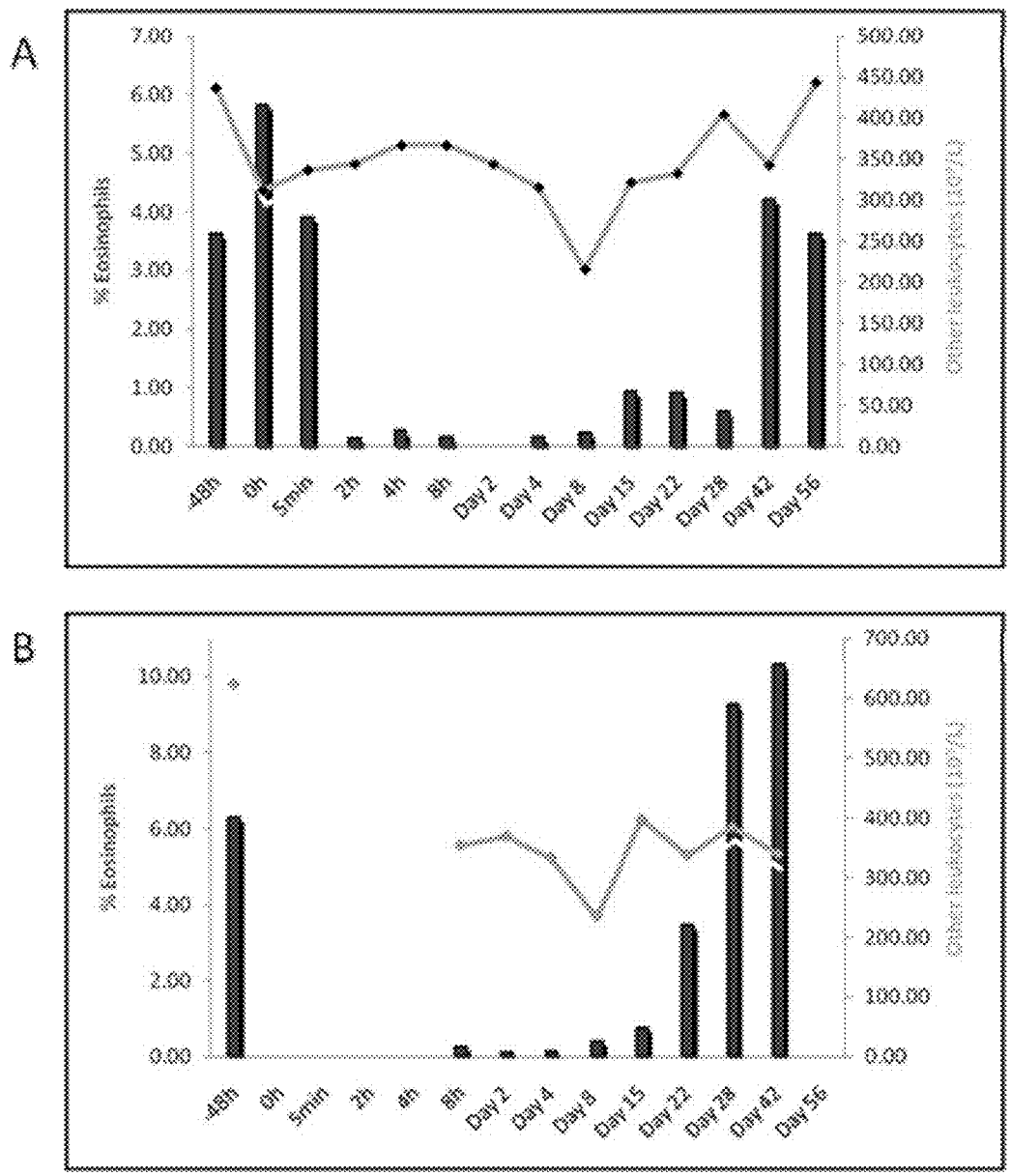
FIG. 9 provides illustrative data showing circulating eosinophil counts of cynomolgus macaques animals dosed with A) 5 mg/kg or B) 1 mg/kg anti-EMR1 antibody.

A single dose of non-fucosylated c1E7 antibody was administered i.v. to two groups of male cynomolgus macaques (n=2) at two dose levels; 1 mg/kg and 5 mg/kg. White blood cells and eosinophils were counted from blood samples taken up to 56 days post-dosing. Circulating eosinophil counts are expressed as percent of total leukocytes in FIG. 9 for animals dosed with A) 5 mg/kg and B) 1 mg/kg antibody. (Data are means from the two animals in each group.) Eosinophils were depleted from the circulation within 2 hours of administration of the antibody at 5 mg/kg and by the time of the first blood sample (taken at 8-hours post-dosing) in the animals treated with 1 mg/kg c1E7. Eosinophil counts returned to the normal range by 28 days post-dosing in the 1 mg/kg group. Recovery of eosinophil counts occurred later in the 5 mg/kg group with mean eosinophil counts returning to normal within 42 days. The total white cell counts were not affected by antibody treatment. Thus, the antibody showed potent selective and reversible depletion of circulating eosinophils.

The following examples are provided by way of illustration only and not by way of limitation. Those of skill in the art will readily recognize a variety of non-critical parameters that could be changed or modified to yield essentially similar results.

All patents, patent applications, accession numbers, and other published reference materials cited in this specification are hereby incorporated herein by reference in their entirety for their disclosures of the subject matter in whose connection they are cited herein.

SEQ ID NO:25 EMR1 Extracellular Domain Amino Acid Sequence

The following is an example of an EMR1 extracellular domain amino acid sequence from GenBank accession number CAA57232.1)

```
  1 MRGFNLLLFW GCCVMHSWEG HIRPTRKPNT KGNNCRDSTL CPAYATCTNT VDSYYCTCKQ

61 GFLSSNGQNH FKDPGVRCKD IDECSQSPQP CGPNSSCKNL SGRYKCSCLD GFSSPTGNDW

121 VPGKPGNFSC TDINECLTSR VCPEHSDCVN SMGSYSCSCQ VGFISRNSTC EDVNECADPR

181 ACPEHATCNN TVGNYSCFCN PGFESSSGHL SCQGLKASCE DIDECTEMCP INSTCTNTPG

241 SYFCTCHPGF APSSGQLNFT DQGVECRDID ECRQDPSTCG PNSICTNALG SYSCGCIVGF

301 HPNPEGSQKD GNFSCQRVLF
```

What is claimed is:

1. An isolated monoclonal anti-epidermal growth factor-like module containing, mucin-like, hormone receptor-like 1 (EMR1) antibody comprising a $V_H$ region and a $V_L$ region, wherein the antibody selectively binds to RDIDECRQDP-STCGPNSI (SEQ ID NO:30).

2. The anti-EMR1 antibody of claim 1, wherein the antibody competes with monoclonal antibody 1E7 for binding to EMR1.

3. The anti-EMR1 antibody of claim 1, wherein the antibody competes with a monoclonal antibody having the same CDR sequences as monoclonal antibody 1E7 for binding to EMR1.

4. The anti-EMR1 antibody of claim 1, wherein the antibody comprises:

a $V_H$ having a CDR3 amino acid sequence IYYRGFDX$_1$ (SEQ ID NO:31), wherein X$_1$ is Q, S, K, or V, a CDR1 amino acid sequence (D/S/N)FG(M/I)H (SEQ ID NO:33), and a CDR2 amino acid sequence VIWSGGST(D/N/Y)YADSVKG (SEQ ID NO:34); and a $V_L$ having a CDR3 amino acid sequence (F/V/T/N)QG(V/S/G/T)H(V/L/P)PLT (SEQ ID NO:35), a CDR1 amino acid sequence (R/K)SSQS(I/L)(V/L)HSNG(N/Y)(N/T)YLE (SEQ ID NO:37) and a CDR2 amino acid sequence R(V/G)SNRAS (SEQ ID NO:38).

5. The anti-EMR1 antibody of claim 4, wherein the $V_H$ has a V-segment sequence of a $V_H$ region of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11; and the $V_L$ has a V-segment sequence of a $V_L$ region of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

6. The antibody of claim 4, wherein the antibody has a $V_H$ region sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11; and a $V_L$ region sequence of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

7. The anti-EMR1 antibody of claim 1, wherein the antibody has:
(a) the heavy chain CDR1, CDR2, and CDR3 of SEQ ID NO:8, SEQ ID NO:4, SEQ ID NO:9, or SEQ ID NO:11, and the light chain CDR1, CDR2, and CDR3 of SEQ ID NO:17;
(b) the heavy chain CDR1, CDR2, and CDR3 of SEQ ID NO:9 and the light chain CDR1, CDR2, and CDR3 of SEQ ID NO:18;
(c) the heavy chain CDR1, CDR2, and CDR3 of SEQ ID NO:6 and the light chain CDR1, CDR2, and CDR3 SEQ ID NO:15;
(d) the heavy CDR1, CDR2, and CDR3 of SEQ ID NO:7 and the light chain CDR1, CDR2, and CDR3 of SEQ ID NO:16;
(e) the heavy chain CDR1, CDR2, and CDR3 of SEQ ID NO:11 and the light chain CDR1, CDR2, and CDR3 of SEQ ID NO:21 or SEQ ID NO:22; or
(f) the heavy chain CDR1, CDR2, and CDR3 of SEQ ID NO:9 and the light chain CDR1, CDR2, and CDR3 of SEQ ID NO:21.

8. An antibody preparation comprising an anti-EMR1 antibody of claim 1, wherein the antibody has a heavy chain constant region that is hypofucosylated or afucosylated.

9. A pharmaceutical composition comprising a physiologically acceptable carrier and an antibody of claim 1.

10. An anti-EMR1 antibody that has a heavy chain and a light chain, wherein the antibody has:

a heavy chain variable region that has a $V_H$ region sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11; and a light chain variable region that has a $V_L$ region sequence of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

* * * * *

SEQUENCE LISTING

```
<160> NUMBER OF SEQ ID NOS: 89

<210> SEQ ID NO 1
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 1

Glu Val Gln Leu Val Glu Ser Gly Gly Gly Val Val Gln Pro Gly Arg
 1               5                  10                  15

Ser Leu Arg Leu Ser Cys Val Val Ser Gly Phe Thr Leu Thr Asp Phe
                20                  25                  30

Gly Ile His Trp Val Arg Gln Ala Pro Gly Lys Gly Leu Glu Trp Val
            35                  40                  45

Ala Val Ile Trp Ser Gly Gly Ser Thr Asp Tyr Ala Asp Ser Val Lys
        50                  55                  60

Gly Arg Phe Thr Ile Ser Arg Asp Asn Ser Lys Asn Thr Val Tyr Leu
 65                  70                  75                  80

Arg Met Asn Ser Leu Arg Ala Glu Asp Thr Pro Val Tyr Tyr Cys Val
                85                  90                  95

Ser Ile Tyr Tyr Arg Gly Phe Asp Ser Trp Gly Gln Gly Thr Thr Val
               100                 105                 110
```

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 2

Gln Val Gln Leu Val Glu Ser Gly Gly Val Val Gln Pro Gly Arg
 1               5                  10                  15

Ser Leu Arg Leu Ser Cys Ala Ala Ser Gly Phe Ser Leu Thr Ser Phe
            20                  25                  30

Gly Ile His Trp Val Arg Gln Ala Pro Gly Lys Gly Leu Glu Trp Val
            35                  40                  45

Gly Val Ile Trp Ser Gly Gly Ser Thr Asn Tyr Ala Asp Ser Val Lys
        50                  55                  60

Gly Arg Phe Thr Ile Ser Arg Asp Asn Ser Lys Asn Thr Val Tyr Leu
65                  70                  75                  80

Arg Met Asn Ser Leu Arg Ala Glu Asp Thr Ala Val Tyr Tyr Cys Val
                85                  90                  95

Ser Ile Tyr Tyr Arg Gly Phe Asp Ser Trp Gly Gln Gly Thr Thr Val
                100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 3

Gln Val Gln Leu Val Glu Ser Gly Gly Val Val Gln Pro Gly Arg
 1               5                  10                  15

Ser Leu Arg Leu Ser Cys Ala Val Ser Gly Phe Ser Leu Thr Asn Phe
            20                  25                  30

Gly Met His Trp Val Arg Gln Ala Pro Gly Lys Gly Leu Glu Trp Val
            35                  40                  45

Gly Val Ile Trp Ser Gly Gly Ser Thr Tyr Tyr Ala Asp Ser Val Lys
        50                  55                  60

Gly Arg Phe Thr Ile Ser Arg Asp Asn Ser Lys Asn Thr Val Tyr Leu
65                  70                  75                  80

Arg Met Asn Ser Leu Arg Ala Glu Asp Thr Ala Val Tyr Tyr Cys Val
                85                  90                  95

Ser Ile Tyr Tyr Arg Gly Phe Asp Ser Trp Gly Gln Gly Thr Thr Val
                100                 105                 110

Thr Val Ser Ser
        115

<210> SEQ ID NO 4
<211> LENGTH: 116

<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody heavy chain variable region

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Phe
            20                  25                  30

Gly Met His Trp Val Arg Gln Ala Pro Gly Lys Gly Leu Glu Trp Val
        35                  40                  45

Ala Val Ile Trp Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Ser Ile Tyr Tyr Arg Gly Phe Asp Gln Trp Gly Gln Gly Thr Thr Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody heavy chain variable region

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Asn Phe
            20                  25                  30

Gly Met His Trp Val Arg Gln Ala Pro Gly Lys Gly Leu Glu Trp Val
        35                  40                  45

Gly Val Ile Trp Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Ile Tyr Tyr Arg Gly Phe Asp Gln Trp Gly Gln Gly Thr Thr Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody heavy chain variable region

```
<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Phe
            20                  25                  30

Gly Met His Trp Val Arg Gln Ala Pro Gly Lys Gly Leu Glu Trp Val
        35                  40                  45

Ala Val Ile Trp Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Ile Tyr Tyr Arg Gly Phe Asp Val Trp Gly Gln Gly Thr Thr Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Ser Phe
            20                  25                  30

Gly Met His Trp Val Arg Gln Ala Pro Gly Lys Gly Leu Glu Trp Val
        35                  40                  45

Ala Val Ile Trp Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Ile Tyr Tyr Arg Gly Phe Asp Val Trp Gly Gln Gly Thr Thr Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Phe
            20                  25                  30
```

```
Gly Met His Trp Val Arg Gln Ala Pro Gly Lys Gly Leu Glu Trp Val
        35                  40                  45

Ala Val Ile Trp Ser Gly Gly Ser Thr Tyr Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Ser Ile Tyr Tyr Arg Gly Phe Asp Val Trp Gly Gln Gly Thr Thr Val
                100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Val Ser Gly Phe Ser Leu Thr Ser Phe
                 20                  25                  30

Gly Met His Trp Val Arg Gln Ala Pro Gly Lys Gly Leu Glu Trp Val
        35                  40                  45

Ala Val Ile Trp Ser Gly Gly Ser Thr Tyr Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Ser Ile Tyr Tyr Arg Gly Phe Asp Gln Trp Gly Gln Gly Thr Thr Val
                100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 10

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ser Phe
                 20                  25                  30

Gly Met His Trp Val Arg Gln Ala Pro Gly Lys Gly Leu Glu Trp Val
        35                  40                  45

Ala Val Ile Trp Ser Gly Gly Ser Thr Asp Tyr Ala Asp Ser Val Lys
 50                  55                  60
```

Gly Arg Phe Thr Ile Ser Arg Asp Asn Ser Lys Asn Thr Val Tyr Leu
65                  70                  75                  80

Arg Met Asn Ser Leu Arg Ala Glu Asp Thr Ala Val Tyr Tyr Cys Val
                85                  90                  95

Ser Ile Tyr Tyr Arg Gly Phe Asp Ser Trp Gly Gln Gly Thr Thr Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody heavy chain variable region

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Phe
            20                  25                  30

Gly Met His Trp Val Arg Gln Ala Pro Gly Lys Gly Leu Glu Trp Val
        35                  40                  45

Ala Val Ile Trp Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Ile Tyr Tyr Cys Ala
                85                  90                  95

Ser Ile Tyr Tyr Arg Gly Phe Asp Gln Trp Gly Gln Gly Thr Thr Val
            100                 105                 110

Thr Val Ser Ser
        115

<210> SEQ ID NO 12
<211> LENGTH: 112
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody light chain variable region

<400> SEQUENCE: 12

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Val His Ser
            20                  25                  30

Asn Gly Asn Asn Tyr Leu Glu Trp Tyr Leu Gln Lys Pro Gly Gln Ser
        35                  40                  45

Pro Gln Leu Leu Ile Tyr Arg Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Arg Leu Glu Ile Lys

<210> SEQ ID NO 13
<211> LENGTH: 112
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody light chain variable region

<400> SEQUENCE: 13

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Glu Trp Tyr Leu Gln Lys Pro Gly Gln Ser
        35                  40                  45

Pro Gln Leu Leu Ile Tyr Arg Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Arg Leu Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody light chain variable region

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Tyr Thr Tyr Leu Glu Trp Tyr Leu Gln Lys Pro Gly Gln Ser
        35                  40                  45

Pro Gln Leu Leu Ile Tyr Arg Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Arg Leu Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody light chain variable region

<400> SEQUENCE: 15

```
Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Ile Leu His Ser
             20                  25                  30

Asn Gly Tyr Thr Tyr Leu Glu Trp Tyr Leu Gln Lys Pro Gly Gln Ser
         35                  40                  45

Pro Gln Leu Leu Ile Tyr Arg Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Gly His Leu Pro Leu Thr Phe Gly Gln Gly Thr Arg Leu Glu Ile Lys
            100                 105                 110
```

```
<210> SEQ ID NO 16
<211> LENGTH: 112
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody light chain variable region

<400> SEQUENCE: 16

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Ser
             20                  25                  30

Asn Gly Tyr Thr Tyr Leu Glu Trp Tyr Leu Gln Lys Pro Gly Gln Ser
         35                  40                  45

Pro Gln Leu Leu Ile Tyr Arg Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Val Pro Leu Thr Phe Gly Gln Gly Thr Arg Leu Glu Ile Lys
            100                 105                 110
```

```
<210> SEQ ID NO 17
<211> LENGTH: 112
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody light chain variable region

<400> SEQUENCE: 17

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Val His Ser
             20                  25                  30

Asn Gly Asn Thr Tyr Leu Glu Trp Tyr Leu Gln Lys Pro Gly Gln Ser
         35                  40                  45

Pro Gln Leu Leu Ile Tyr Arg Val Ser Asn Arg Ala Ser Gly Val Pro
 50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Val Pro Leu Thr Phe Gly Gln Gly Thr Arg Leu Glu Ile Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody light chain variable region

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Tyr Thr Tyr Leu Glu Trp Tyr Leu Gln Lys Pro Gly Gln Ser
        35                  40                  45

Pro Gln Leu Leu Ile Tyr Arg Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Val Pro Leu Thr Phe Gly Gln Gly Thr Arg Leu Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody light chain variable region

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Glu Trp Tyr Leu Gln Lys Pro Gly Gln Ser
        35                  40                  45

Pro Gln Leu Leu Ile Tyr Arg Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Gly
                85                  90                  95

Ser His Val Pro Leu Thr Phe Gly Gln Gly Thr Arg Leu Glu Ile Lys
            100                 105                 110

<210> SEQ ID NO 20
<211> LENGTH: 112
<212> TYPE: PRT

<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody light chain variable region

<400> SEQUENCE: 20

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Glu Trp Tyr Leu Gln Lys Pro Gly Gln Ser
        35                  40                  45

Pro Gln Leu Leu Ile Tyr Arg Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Arg Leu Glu Ile Lys
            100                 105                 110
```

<210> SEQ ID NO 21
<211> LENGTH: 112
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody light chain variable region

<400> SEQUENCE: 21

```
Asp Ile Phe Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Val Pro Leu Thr Phe Gly Gln Gly Thr Arg Leu Glu Ile Lys
            100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: synthetic anti-EGF-like module containing, mucin-like, hormone receptor-like 1 (EMR1) mouse monoclonal antibody light chain variable region

<400> SEQUENCE: 22

```
Asp Ile Phe Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30
```

```
Asn Gly Tyr Thr Tyr Leu Glu Trp Tyr Leu Gln Lys Pro Gly Gln Ser
            35                  40                  45

Pro Gln Leu Leu Ile Tyr Arg Val Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Val Pro Leu Thr Phe Gly Gln Gly Thr Arg Leu Glu Ile Lys
            100                 105                 110

<210> SEQ ID NO 23
<211> LENGTH: 116
<212> TYPE: PRT
<213> ORGANISM: Mus sp.
<220> FEATURE:
<223> OTHER INFORMATION: anti-EGF-like module containing, mucin-like,
      hormone receptor-like 1 (EMR1) mouse monoclonal
      antibody 19-1E7 heavy chain variable region
      (19-1E7 Vh)

<400> SEQUENCE: 23

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Asn Phe
             20                  25                  30

Gly Ile His Trp Val Arg Gln Pro Pro Gly Lys Gly Leu Glu Trp Leu
         35                  40                  45

Gly Val Ile Trp Ser Gly Gly Gly Thr Asn Tyr Asn Ser Ala Leu Met
     50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Ile Tyr Tyr Cys Val
                 85                  90                  95

Ser Ile Tyr Tyr Arg Gly Phe Asp Ser Trp Gly Gln Gly Thr Thr Leu
            100                 105                 110

Thr Val Ser Ser
        115

<210> SEQ ID NO 24
<211> LENGTH: 112
<212> TYPE: PRT
<213> ORGANISM: Mus sp.
<220> FEATURE:
<223> OTHER INFORMATION: anti-EGF-like module containing, mucin-like,
      hormone receptor-like 1 (EMR1) mouse monoclonal
      antibody 19-1E7 light chain variable region
      (19-1E7 Vk)

<400> SEQUENCE: 24

Asp Val Phe Met Thr Gln Ala Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
            35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
```

```
65                  70                  75                  80
Ser Arg Val Glu Ala Glu Asp Leu Gly Val Tyr Tyr Cys Phe Gln Gly
                85                  90                  95

Ser His Val Pro Leu Thr Phe Gly Ala Gly Thr Arg Leu Glu Leu Lys
              100                 105                 110

<210> SEQ ID NO 25
<211> LENGTH: 320
<212> TYPE: PRT
<213> ORGANISM: Artificial Sequence
<220> FEATURE:
<223> OTHER INFORMATION: synthetic EGF-like module containing, mucin-like,
      hormone receptor-like 1 (EMR1) extracellular domain

<400> SEQUENCE: 25

Met Arg Gly Phe Asn Leu Leu Phe Trp Gly Cys Cys Val Met His
 1               5                  10                  15

Ser Trp Glu Gly His Ile Arg Pro Thr Arg Lys Pro Asn Thr Lys Gly
                20                  25                  30

Asn Asn Cys Arg Asp Ser Thr Leu Cys Pro Ala Tyr Ala Thr Cys Thr
               35                  40                  45

Asn Thr Val Asp Ser Tyr Tyr Cys Thr Cys Lys Gln Gly Phe Leu Ser
 50                  55                  60

Ser Asn Gly Gln Asn His Phe Lys Asp Pro Gly Val Arg Cys Lys Asp
65                  70                  75                  80

Ile Asp Glu Cys Ser Gln Ser Pro Gln Pro Cys Gly Pro Asn Ser Ser
                85                  90                  95

Cys Lys Asn Leu Ser Gly Arg Tyr Lys Cys Ser Cys Leu Asp Gly Phe
              100                 105                 110

Ser Ser Pro Thr Gly Asn Asp Trp Val Pro Gly Lys Pro Gly Asn Phe
              115                 120                 125

Ser Cys Thr Asp Ile Asn Glu Cys Leu Thr Ser Arg Val Cys Pro Glu
              130                 135                 140

His Ser Asp Cys Val Asn Ser Met Gly Ser Tyr Ser Cys Ser Cys Gln
145                 150                 155                 160

Val Gly Phe Ile Ser Arg Asn Ser Thr Cys Glu Asp Val Asn Glu Cys
                165                 170                 175

Ala Asp Pro Arg Ala Cys Pro Glu His Ala Thr Cys Asn Asn Thr Val
              180                 185                 190

Gly Asn Tyr Ser Cys Phe Cys Asn Pro Gly Phe Glu Ser Ser Ser Gly
              195                 200                 205

His Leu Ser Cys Gln Gly Leu Lys Ala Ser Cys Glu Asp Ile Asp Glu
              210                 215                 220

Cys Thr Glu Met Cys Pro Ile Asn Ser Thr Cys Thr Asn Thr Pro Gly
225                 230                 235                 240

Ser Tyr Phe Cys Thr Cys His Pro Gly Phe Ala Pro Ser Ser Gly Gln
                245                 250                 255

Leu Asn Phe Thr Asp Gln Gly Val Glu Cys Arg Asp Ile Asp Glu Cys
              260                 265                 270

Arg Gln Asp Pro Ser Thr Cys Gly Pro Asn Ser Ile Cys Thr Asn Ala
              275                 280                 285

Leu Gly Ser Tyr Ser Cys Gly Cys Ile Val Gly Phe His Pro Asn Pro
              290                 295                 300

Glu Gly Ser Gln Lys Asp Gly Asn Phe Ser Cys Gln Arg Val Leu Phe
305                 310                 315                 320
```

```
<210> SEQ ID NO 26
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody 19-1E7 heavy chain variable
      region CDR2

<400> SEQUENCE: 26

Val Ile Trp Ser Gly Gly Thr Asn Tyr Asn Ser Ala Leu Met Ser
 1               5                  10                  15

<210> SEQ ID NO 27
<211> LENGTH: 17
<212> TYPE: PRT
<213> ORGANISM: Artificial Sequence
<220> FEATURE:
<223> OTHER INFORMATION: synthetic mouse heavy chain variable region
      germ-line Vh3-33 segment

<400> SEQUENCE: 27

Val Ile Trp Tyr Asp Gly Ser Asn Lys Tyr Tyr Ala Asp Ser Val Lys
 1               5                  10                  15

Gly

<210> SEQ ID NO 28
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1) mouse
      monoclonal antibody 19-1E7 light chain variable
      region CDR1/FR1

<400> SEQUENCE: 28

Arg Ser Ser Gln Ser Ile Val His Ser Asn Gly Asn Thr Tyr Leu Glu
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: synthetic mouse light chain variable region
      CDR1 of germ-line VkII A3 segment

<400> SEQUENCE: 29

Arg Ser Ser Gln Ser Leu Leu His Ser Asn Gly Tyr Asn Tyr Leu Asp
 1               5                  10                  15

<210> SEQ ID NO 30
<211> LENGTH: 18
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      271-288, c1E7 epitope

<400> SEQUENCE: 30

Arg Asp Ile Asp Glu Cys Arg Gln Asp Pro Ser Thr Cys Gly Pro Asn
 1               5                  10                  15

Ser Ile
```

<210> SEQ ID NO 31
<211> LENGTH: 8
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR3 (CDRH3, V-H CDR3)
<220> FEATURE:
<221> NAME/KEY: VARIANT
<222> LOCATION: (8)...(8)
<223> OTHER INFORMATION: Xaa = Gln, Ser, Lys or Val

<400> SEQUENCE: 31

Ile Tyr Tyr Arg Gly Phe Asp Xaa
 1               5

<210> SEQ ID NO 32
<211> LENGTH: 8
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR3 (CDRH3, V-H CDR3)
<220> FEATURE:
<221> NAME/KEY: VARIANT
<222> LOCATION: (8)...(8)
<223> OTHER INFORMATION: Xaa = Gln, Ser or Val

<400> SEQUENCE: 32

Ile Tyr Tyr Arg Gly Phe Asp Xaa
 1               5

<210> SEQ ID NO 33
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)
<220> FEATURE:
<221> NAME/KEY: VARIANT
<222> LOCATION: (1)...(1)
<223> OTHER INFORMATION: Xaa = Asp, Ser or Asn
<220> FEATURE:
<221> NAME/KEY: VARIANT
<222> LOCATION: (4)...(4)
<223> OTHER INFORMATION: Xaa = Met or Ile

<400> SEQUENCE: 33

Xaa Phe Gly Xaa His
 1               5

<210> SEQ ID NO 34
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR2 (CDRH2, V-H CDR2)
<220> FEATURE:
<221> NAME/KEY: VARIANT
<222> LOCATION: (9)...(9)
<223> OTHER INFORMATION: Xaa = Asp, Asn or Tyr

```
<400> SEQUENCE: 34

Val Ile Trp Ser Gly Gly Ser Thr Xaa Tyr Ala Asp Ser Val Lys Gly
 1               5                  10                  15

<210> SEQ ID NO 35
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)
<220> FEATURE:
<221> NAME/KEY: VARIANT
<222> LOCATION: (1)...(1)
<223> OTHER INFORMATION: Xaa = Phe, Val, Thr or Asn
<220> FEATURE:
<221> NAME/KEY: VARIANT
<222> LOCATION: (4)...(4)
<223> OTHER INFORMATION: Xaa = Val, Ser, Gly or Thr
<220> FEATURE:
<221> NAME/KEY: VARIANT
<222> LOCATION: (6)...(6)
<223> OTHER INFORMATION: Xaa = Val, Leu or Pro

<400> SEQUENCE: 35

Xaa Gln Gly Xaa His Xaa Pro Leu Thr
 1               5

<210> SEQ ID NO 36
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)
<220> FEATURE:
<221> NAME/KEY: VARIANT
<222> LOCATION: (1)...(1)
<223> OTHER INFORMATION: Xaa = Phe, Val or Thr
<220> FEATURE:
<221> NAME/KEY: VARIANT
<222> LOCATION: (4)...(4)
<223> OTHER INFORMATION: Xaa = Ser, Gly or Thr
<220> FEATURE:
<221> NAME/KEY: VARIANT
<222> LOCATION: (6)...(6)
<223> OTHER INFORMATION: Xaa = Val or Leu

<400> SEQUENCE: 36

Xaa Gln Gly Xaa His Xaa Pro Leu Thr
 1               5

<210> SEQ ID NO 37
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)
<220> FEATURE:
<221> NAME/KEY: VARIANT
<222> LOCATION: (1)...(1)
<223> OTHER INFORMATION: Xaa = Arg or Lys
<220> FEATURE:
<221> NAME/KEY: VARIANT
<222> LOCATION: (6)...(6)
```

```
<223> OTHER INFORMATION: Xaa = Ile or Leu
<220> FEATURE:
<221> NAME/KEY: VARIANT
<222> LOCATION: (7)...(7)
<223> OTHER INFORMATION: Xaa = Val or Leu
<220> FEATURE:
<221> NAME/KEY: VARIANT
<222> LOCATION: (12)...(12)
<223> OTHER INFORMATION: Xaa = Asn or Tyr
<220> FEATURE:
<221> NAME/KEY: VARIANT
<222> LOCATION: (13)...(13)
<223> OTHER INFORMATION: Xaa = Asn or Thr

<400> SEQUENCE: 37

Xaa Ser Ser Gln Ser Xaa Xaa His Ser Asn Gly Xaa Xaa Tyr Leu Glu
 1               5                  10                  15

<210> SEQ ID NO 38
<211> LENGTH: 7
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR2 (CDRL2, V-L CDR2)
<220> FEATURE:
<221> NAME/KEY: VARIANT
<222> LOCATION: (2)...(2)
<223> OTHER INFORMATION: Xaa = Val or Gly

<400> SEQUENCE: 38

Arg Xaa Ser Asn Arg Ala Ser
 1               5

<210> SEQ ID NO 39
<211> LENGTH: 8
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR3 (CDRH3, V-H CDR3)

<400> SEQUENCE: 39

Ile Tyr Tyr Arg Gly Phe Asp Gln
 1               5

<210> SEQ ID NO 40
<211> LENGTH: 8
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR3 (CDRH3, V-H CDR3)

<400> SEQUENCE: 40

Ile Tyr Tyr Arg Gly Phe Asp Ser
 1               5

<210> SEQ ID NO 41
<211> LENGTH: 8
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
```

```
                      monoclonal antibody heavy chain variable region
                      CDR3 (CDRH3, V-H CDR3)

<400> SEQUENCE: 41

Ile Tyr Tyr Arg Gly Phe Asp Val
 1               5

<210> SEQ ID NO 42
<211> LENGTH: 8
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR3 (CDRH3, V-H CDR3)

<400> SEQUENCE: 42

Ile Tyr Tyr Arg Gly Phe Asp Lys
 1               5

<210> SEQ ID NO 43
<211> LENGTH: 11
<212> TYPE: PRT
<213> ORGANISM: Artificial Sequence
<220> FEATURE:
<223> OTHER INFORMATION: synthetic human heavy chain FR4 germline JH6
      sequence

<400> SEQUENCE: 43

Trp Gly Gln Gly Thr Thr Val Thr Val Ser Ser
 1               5                  10

<210> SEQ ID NO 44
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)
<220> FEATURE:
<221> NAME/KEY: VARIANT
<222> LOCATION: (4)...(4)
<223> OTHER INFORMATION: Xaa = Met or Ile

<400> SEQUENCE: 44

Gln Phe Gly Xaa His
 1               5

<210> SEQ ID NO 45
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)

<400> SEQUENCE: 45

Asp Phe Gly Met His
 1               5

<210> SEQ ID NO 46
<211> LENGTH: 5
<212> TYPE: PRT
<213> ORGANISM: Artificial Sequence
```

```
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)

<400> SEQUENCE: 46

Asp Phe Gly Ile His
1               5

<210> SEQ ID NO 47
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)

<400> SEQUENCE: 47

Ser Phe Gly Met His
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)

<400> SEQUENCE: 48

Ser Phe Gly Ile His
1               5

<210> SEQ ID NO 49
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)

<400> SEQUENCE: 49

Asn Phe Gly Met His
1               5

<210> SEQ ID NO 50
<211> LENGTH: 5
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR1 (CDRH1, V-H CDR1)

<400> SEQUENCE: 50

Asn Phe Gly Ile His
1               5

<210> SEQ ID NO 51
<211> LENGTH: 16
<212> TYPE: PRT
```

-continued

```
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR2 (CDRH2, V-H CDR2)

<400> SEQUENCE: 51

Val Ile Trp Ser Gly Gly Ser Thr Asp Tyr Ala Asp Ser Val Lys Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR2 (CDRH2, V-H CDR2)

<400> SEQUENCE: 52

Val Ile Trp Ser Gly Gly Ser Thr Asn Tyr Ala Asp Ser Val Lys Gly
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody heavy chain variable region
      CDR2 (CDRH2, V-H CDR2)

<400> SEQUENCE: 53

Val Ile Trp Ser Gly Gly Ser Thr Tyr Tyr Ala Asp Ser Val Lys Gly
1               5                   10                  15

<210> SEQ ID NO 54
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 54

Phe Gln Gly Ser His Val Pro Leu Thr
1               5

<210> SEQ ID NO 55
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 55

Ser Gln Gly Ser His Val Pro Leu Thr
1               5

<210> SEQ ID NO 56
<211> LENGTH: 9
```

```
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 56

Asn Gln Gly Ser His Val Pro Leu Thr
 1               5

<210> SEQ ID NO 57
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 57

Phe Gln Gly Ser His Thr Pro Leu Thr
 1               5

<210> SEQ ID NO 58
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 58

Phe Gln Gly Val His Val Pro Leu Thr
 1               5

<210> SEQ ID NO 59
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 59

Phe Gln Ser Ser His Val Pro Leu Thr
 1               5

<210> SEQ ID NO 60
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 60

Ser Gln Gly Ser His Val Pro Leu Thr
 1               5

<210> SEQ ID NO 61
```

```
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 61

Phe Gln Gly Ser His Pro Pro Leu Thr
 1               5

<210> SEQ ID NO 62
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 62

Val Gln Gly Thr His Val Pro Leu Thr
 1               5

<210> SEQ ID NO 63
<211> LENGTH: 9
<212> TYPE: PRT
<213> ORGANISM: Artificial Sequence
<220> FEATURE:
<223> OTHER INFORMATION: synthetic mouse monoclonal antibody light
      chain variable region (V-L) F4 region

<400> SEQUENCE: 63

Phe Gly Gln Gly Thr Arg Glu Ile Lys
 1               5

<210> SEQ ID NO 64
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 64

Arg Ser Ser Gln Ser Ile Val His Ser Asn Gly Asn Asn Tyr Leu Glu
 1               5                  10                  15

<210> SEQ ID NO 65
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 65

Lys Ser Ser Gln Ser Ile Val His Ser Asn Gly Asn Asn Tyr Leu Glu
 1               5                  10                  15

<210> SEQ ID NO 66
<211> LENGTH: 16
```

```
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 66

Arg Ser Ser Gln Ser Leu Val His Ser Asn Gly Asn Asn Tyr Leu Glu
 1               5                  10                  15

<210> SEQ ID NO 67
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 67

Lys Ser Ser Gln Ser Leu Val His Ser Asn Gly Asn Asn Tyr Leu Glu
 1               5                  10                  15

<210> SEQ ID NO 68
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 68

Arg Ser Ser Gln Ser Leu Val His Ser Asn Gly Tyr Thr Tyr Leu Glu
 1               5                  10                  15

<210> SEQ ID NO 69
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 69

Arg Ser Ser Gln Ser Leu Val His Ser Asn Gly Asn Thr Tyr Leu Glu
 1               5                  10                  15

<210> SEQ ID NO 70
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 70

Arg Ser Ser Gln Ser Leu Val His Ser Asn Gly Tyr Asn Tyr Leu Glu
 1               5                  10                  15

<210> SEQ ID NO 71
```

```
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 71

Lys Ser Ser Gln Ser Leu Val His Ser Asn Gly Tyr Thr Tyr Leu Glu
 1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 72

Lys Ser Ser Gln Ser Leu Val His Ser Asn Gly Tyr Thr Tyr Leu Glu
 1               5                  10                  15

<210> SEQ ID NO 73
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 73

Lys Ser Ser Gln Ser Leu Val His Ser Asn Gly Asn Thr Tyr Leu Glu
 1               5                  10                  15

<210> SEQ ID NO 74
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 74

Lys Ser Ser Gln Ser Leu Val His Ser Asn Gly Tyr Asn Tyr Leu Glu
 1               5                  10                  15

<210> SEQ ID NO 75
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 75

Lys Ser Ser Gln Ser Leu Val His Ser Asn Gly Tyr Thr Tyr Leu Glu
 1               5                  10                  15
```

```
<210> SEQ ID NO 76
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 76

Lys Ser Ser Gln Ser Ile Leu His Ser Asn Gly Tyr Thr Tyr Leu Glu
 1               5                  10                  15

<210> SEQ ID NO 77
<211> LENGTH: 16
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR1 (CDRL1, V-L CDR1)

<400> SEQUENCE: 77

Lys Ser Ser Gln Ser Leu Leu His Ser Asn Gly Tyr Thr Tyr Leu Glu
 1               5                  10                  15

<210> SEQ ID NO 78
<211> LENGTH: 7
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR2 (CDRL2, V-L CDR2)

<400> SEQUENCE: 78

Arg Val Ser Asn Arg Ala Ser
 1               5

<210> SEQ ID NO 79
<211> LENGTH: 7
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR2 (CDRL2, V-L CDR2)

<400> SEQUENCE: 79

Arg Gly Ser Asn Arg Ala Ser
 1               5

<210> SEQ ID NO 80
<211> LENGTH: 10
<212> TYPE: PRT
<213> ORGANISM: Artificial Sequence
<220> FEATURE:
<223> OTHER INFORMATION: synthetic mouse monoclonal antibody light
      chain variable region (V-L) F4 region

<400> SEQUENCE: 80

Phe Gly Gln Gly Thr Arg Leu Glu Ile Lys
 1               5                  10

<210> SEQ ID NO 81
```

<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, V-L CDR3)

<400> SEQUENCE: 81

Asn Gln Gly Thr His Val Pro Leu Thr
1               5

<210> SEQ ID NO 82
<211> LENGTH: 27
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      271-297, Peptide 1

<400> SEQUENCE: 82

Arg Asp Ile Asp Glu Cys Arg Gln Asp Pro Ser Thr Cys Gly Pro Asn
1               5                   10                  15

Ser Ile Cys Thr Asn Ala Leu Gly Ser Tyr Ser
            20                  25

<210> SEQ ID NO 83
<211> LENGTH: 28
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      297-324, Peptide 2

<400> SEQUENCE: 83

Ser Cys Gly Cys Ile Ala Gly Phe His Pro Asn Pro Glu Gly Ser Gln
1               5                   10                  15

Lys Asp Gly Asn Phe Ser Cys Gln Arg Val Asn Ser
            20                  25

<210> SEQ ID NO 84
<211> LENGTH: 26
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      285-310, Peptide 3

<400> SEQUENCE: 84

Pro Asn Ser Ile Cys Thr Asn Ala Leu Gly Ser Tyr Ser Cys Gly Cys
1               5                   10                  15

Ile Ala Gly Phe His Pro Asn Pro Glu Gly
            20                  25

<210> SEQ ID NO 85
<211> LENGTH: 20
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      271-290, Peptide 4

<400> SEQUENCE: 85

Arg Asp Ile Asp Glu Cys Arg Gln Asp Pro Ser Thr Cys Gly Pro Asn
 1               5                   10                  15

Ser Ile Cys Thr
            20

<210> SEQ ID NO 86
<211> LENGTH: 21
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      277-297, Peptide 5

<400> SEQUENCE: 86

Arg Gln Asp Pro Ser Thr Cys Gly Pro Asn Ser Ile Cys Thr Asn Ala
 1               5                   10                  15

Leu Gly Ser Tyr Ser
            20

<210> SEQ ID NO 87
<211> LENGTH: 18
<212> TYPE: PRT
<213> ORGANISM: Artificial Sequence
<220> FEATURE:
<223> OTHER INFORMATION: synthetic EGF-like module containing,
      mucin-like, hormone receptor-like 1 (EMR1) sequence epidermal
      growth factor-like domain 6 (ELD-6) positions
      273-290, Peptide 6

<400> SEQUENCE: 87

Ile Asp Glu Cys Arg Gln Asp Pro Ser Thr Cys Gly Pro Asn Ser Ile
 1               5                   10                  15

Cys Thr

<210> SEQ ID NO 88
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, LCDR3)

<400> SEQUENCE: 88

Thr Gln Gly Ser His Val Pro Leu Thr
 1               5

<210> SEQ ID NO 89
<211> LENGTH: 9
<212> TYPE: PRT
<213> ORGANISM: Artificial Sequence
<220> FEATURE:
<223> OTHER INFORMATION: synthetic anti-EGF-like module containing,
      mucin-like, hormone receptor-like 1 (EMR1)
      monoclonal antibody light chain variable region
      CDR3 (CDRL3, LCDR3)

<400> SEQUENCE: 89

Val Gln Gly Gly His Leu Pro Leu Thr
1               5